US008003628B2

(12) United States Patent
Greene et al.

(10) Patent No.: US 8,003,628 B2
(45) Date of Patent: Aug. 23, 2011

(54) METHODS OF INHIBITING OSTEOCLAST ACTIVITY

(75) Inventors: Mark I Greene, Penn Valley, PA (US); Ramachandran Murali, Swarthmore, PA (US); Masahiko Kinosaki, Tochigi (JP)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/488,868

(22) Filed: Jun. 22, 2009

(65) Prior Publication Data
US 2009/0306030 A1 Dec. 10, 2009

Related U.S. Application Data

(62) Division of application No. 10/625,073, filed on Jul. 22, 2003, now Pat. No. 7,566,741, which is a division of application No. 09/628,665, filed on Jul. 28, 2000, now Pat. No. 6,673,771.

(60) Provisional application No. 60/146,094, filed on Jul. 28, 1999.

(51) Int. Cl.
A61K 31/585 (2006.01)
A61K 31/015 (2006.01)
A61K 31/565 (2006.01)
A61K 31/58 (2006.01)
A61P 19/00 (2006.01)

(52) U.S. Cl. ......... 514/175; 514/748; 514/182; 514/172

(58) Field of Classification Search .................. 514/175, 514/748, 182, 172, 13
See application file for complete search history.

(56) References Cited

U.S. PATENT DOCUMENTS

| | | | |
|---|---|---|---|
| 4,215,051 A | 7/1980 | Schroeder et al. |
| 4,946,778 A | 8/1990 | Ladner et al. |
| 5,470,952 A | 11/1995 | Stahl et al. |
| 5,849,865 A | 12/1998 | Cheng et al. |
| 5,869,452 A | 2/1999 | Ng et al. |
| 5,955,425 A | 9/1999 | Morley et al. |
| 5,985,832 A | 11/1999 | Roodman et al. |
| 6,171,860 B1 | 1/2001 | Baker et al. |
| 6,239,157 B1 | 5/2001 | Mbalaviele |
| 6,673,771 B1 | 1/2004 | Greene et al. |
| 7,566,741 B2 | 7/2009 | Greene et al. |

FOREIGN PATENT DOCUMENTS

| | | |
|---|---|---|
| EP | 0 045 665 A1 | 2/1982 |
| EP | 0 784 093 | 7/1997 |
| WO | WO 98/28426 | 7/1998 |
| WO | WO 98/53842 | 12/1998 |
| WO | WO 99/58674 | 11/1999 |
| WO | WO 00/01349 | 1/2000 |
| WO | WO 00/15807 | 3/2000 |
| WO | WO 01/08699 | 2/2001 |

OTHER PUBLICATIONS

Ahmed et al., The Journal of Biological Chemistry, 250(21):8477-8482, Nov. 1975.
Albericio et al., Int. J. Peptide Protein Res. 26:92-97, 1985.
Anderson et al. Nature, vol. 390, pp. 175-179, Nov. 13, 1997.
Banner et al., Cell, 73:431-445, May 1993.
Beutler et al., Science, 264:667-668, Apr. 1994.
Beutler et al., Annals of The New York Academy of Sciences, 730:118-133, 1994.
Bowie et al. Science, vol. 247, pp. 1306-1310, 1990.
Brisson et al., Nature, 310:511-514, Aug. 1984.
Broglie et al., Science 224:838-843, May 1984.
Bucay et al., Genes Dev., 12(9):1260-1268, 1998.
Cole et al., Monoclonal Antibodies and Cancer Therapy, 77-96, Jan.-Feb. 1985.
Coruzzi et al., The EMBO Journal 3(8):1671-1679.
Cote et al., Proc. Natl. Acad. Sci. USA, 80:2026-2030, 1983.
Doring et al., Molecular Immunology, 31(14):1059-1067, 1994.
Filvaroff, Current Biology, 8:R679-682, 1998.
Fox et al. Biochem. Biphys. Res. Comm., vol. 276, pp. 868-872, 2000.
Fingl et al., "General Principles," In: The Pharmacological Basis of Therapeutics, Chapter 1, 1-46, 1975.
Fuller, K., et al., "Trance is necessary and sufficient for osteoblastmediated activation of bone resorption in osteoclasts," Database Chemical Abstracts on STN, No. 129:314804, Abstract, J. Exp. Med., 1998, 188(5), 997-1001.
Gruss et al., Cytokines and Molecular Therapy 1:75-105, May 1995.
Gurley, et al., Molecular and Cellular Biology, 6:559-565, Feb. 1986.
Habeeb, A.F.S.A., Analytical Biochemistry, 56:60-65, 1973.
Hann et al., J. Chem. Soc. Perkin Trans., 1, 307-314, 1982.
Holladay et al., Tetrahedron Letters, 24(41):4401-4404, 1983.
Houghten et al. Cell, vol. 93, pp. 165-176, Apr. 17, 1998.
Houghten et al., Vaccines 86, Cold Spring Harbor Laboratory, pp. 21-25, 1986.
Hruby et al., Life Sciences, 31:189-199, 1982.
Hudson et al. Int. J. Protein Res., 14:177-185, 1979.
Huse, et al., Science, 246:1275-1281, Dec. 1989.

(Continued)

*Primary Examiner* — Paddy Padmanabhan
*Assistant Examiner* — Sahar Javanmard
(74) *Attorney, Agent, or Firm* — Woodcock Washburn, LLP

(57) ABSTRACT

Methods of inhibiting osteoclastogenesis and the activity of osteoclasts are disclosed. Methods of treating patients who have diseases characterized bone loss are disclosed. According to the methods, an amount of a TRANCE/RANK inhibitor effective to inhibit osteoclastogenesis is administered to the patient. Pharmaceutical compositions which comprise TRANCE/RANK inhibitor in an amount effective to inhibit osteoclastogenesis. Methods of modulating dendritic cell maturation, T cell proliferation, and/or CD40 receptor systems in an individual are disclosed. The methods comprise the step of administering to the individual an amount of a TRANCE/RANK inhibitor effective to modulating dendritic cell maturation, T cell proliferation, and/or CD40 receptor systems.

7 Claims, No Drawings

OTHER PUBLICATIONS

Jennings-White et al., Tetrahedron Letters, 23(25):2533-2534, 1982.
Kamber et al., Helvetica Chimica Acta, 63(Fasc. 4):899-915, 1980.
Kitazawa et al., J. of Clinical Investigation, 94:2397-2407, Dec. 1994.
Kobayashi et al., J. Exp. Med., vol. 191, No. 2, 275-285, 2000.
Kohler et al., Nature, 256:495-497, 1975.
Kong et al., Immunology and Cell Biology, 77:188-193, Jan. 1999.
Kong et al., Nature, 397:315-323, 1999.
Kornak et al., Cell, 104:205-215, 2001.
Kozbor et al., Immunology Today, 4(3):72-79, 1983.
Lacey et al., Amer. J. of Pathology, 157(2):435-448, 2000.
Li Y.P. et al., Nature Genetics, 23:447-451, 1999.
Li J. et al., PNAS, 97(4):1566-1571, 2000.
Livingstone, David M., Methods in Enzymology, Affinity Techniques, 723-731, 1974.
Logan et al., Proc. Natl. Acad. Sci. USA, 81:3655-3659, Jun. 1984.
Mackett et al., Proc. Natl. Acad. Sci. USA 79:7415-7519, Dec. 1982.
Mackett et al., Journal of Virology, 49(3):857-864, Mar. 1984.
McOsker et al., J. Bone & Mineral Research, Twelfth Annual Meeting of the American Societ for Bone and Mineral Research, 5(Supp 2):S105, No. 128, Abstract, Aug. 28-31, 1990.
Moore et al., Techniques in Protein Chemistry VII, Marsak (ed.) 81-91, 1996.
Morley, J.S., Trends Pharm. Sci., 463-468, Dec. 1980.
Morrison et al., Proc. Natl. Acad. Sci. USA, 81:6851-6855, Nov. 1984.
Mortensen et al., J. Clinical Endrocrinology and Metabolism, 83(2):396-402, 1998.
Nakagawa, N., e tal., "Rank is the essential signaling receptor for osteoclast differentiation factor in osteoclastogensis" Database Chemical Abstracts on STN, No. 130:166173, Abstract, Biochem. Biophys. Res. Commun., 1998, 253(2), 395-400.
Neuberger et al., Nature, 312:604-608, Dec. 1984.
Nicholson et al., J. Clinical Investigation, 78:355-360, Aug. 1986.
Panicali et al., Proc. Natl. Acad. Sci. USA, 79:4927-4931, Aug. 1982.
Peppel et al., J. Exp. Med., 174:1483-1489, Dec. 1991.
Ponder et al., J. Mol. Biol., 193:775-791, 1987.
Scimeca, J.C., Bone, 26(3):207-213, 2000.
Shalhoub, V. et al., British J. of Haematology, 111:501-512, 2000.
Shalhoub et al., J. Cellular Biochem., 72(2):251-261, 1999.
Sietsema et al., Drugs Exptl. Clin. Res., XV(9):389-396, 1989.
Simonet et al., Osteoprotegerin: A Novel Secreted Protein Involved in the Regulation of Bone Density, Cell, 1997, vol. 89, pp. 309-319.
Singer et al., J. Clinical Endocrinology and Metabolism, 83(6):1906-1910, 1998.
Siris et al., J. Bone and Mineral Research, 13(6):1032-1038, 1998.
Smith et al., Journal of Virology, 46:584-593, May 1983.
Spatola, A. F., Chemistry and Biochemistry of Amino Acids, Peptides, and Proteins, 7:267-357, 1983.
Spatola et al., Life Sciences, 38:1243-1249, 1986.
Suda et al., Endocrine Reviews 20(3):345-357, Jun. 1999.
Suda et al., Novartis Found Symp, 232: 235, 2001 (Abstract).
Takamatsu et al., EMBRO Journal, 6(2):307-311, 1987.
Takasaki et al., Nature Biotechnology, 15:1266-1270, 1997.
Takeda et al., Nature 314:452-454, 1985.
Tam et al., Synthesis, 955-957, Dec. 1979.
Van Beek E., J. Bone and Mineral Research, 11(10):1492-1497, 1996.
Weitzmann et al., J. of Bone and Mineral Research, 16(2):328-337, 2001.
Williams et al., Immunology, 84:433-439, 1995.
Wong et al. Journal of Leukocyte Biology, 65:715-724, Jun. 1999.
Yamaguchi et al., J. of Biological Chemisty, 273(9):5177-5123, Feb. 28, 1998.
Yasuda et al. Proc. Natl. Acad. Sci. USA., vol. 95 pp. 3597-3602, Mar. 1998.
Zhang et al., Nature Biotechnology, 14:472-475, Apr. 1996.
Zhang et al., Nature Biotechnology, 15:150-154, 1997.
Wong, B.R. et al., "Trance (Tumor Necrosis Factor [TNF]-related Activation-induced Cytokine), a New TNF Family Member Predominantly Expressed in T cells, Is a Dendritic Cell-specific Survival Factor," J. Exp. Med., Dec. 15, 1997, 186(12), 2075-2080.

SEQUENCE LISTING

```
<160> NUMBER OF SEQ ID NOS: 34

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 1

Asp Arg Gly Trp Ala
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 2

Asp Gly Asp Leu Ala Thr
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 3

Ser Asp Phe Ala Thr Glu
  1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 4

Val Thr Lys Thr Ser Ile Lys Ile Pro Ser Ser His
  1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 5

Thr Lys Thr Ser Ile Lys Ile Pro Ser Ser His
  1               5                  10

<210> SEQ ID NO 6
<211> LENGTH: 10
<212> TYPE: PRT
<213> ORGANISM: Artificial Sequence
<220> FEATURE:
```

```
<223> OTHER INFORMATION: Description of Artificial Sequence: Novel
      Sequence

<400> SEQUENCE: 6

Lys Thr Ser Ile Lys Ile Pro Ser Ser His
 1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 7

Tyr Trp Ser Asn Ser Glu Phe
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 8

Tyr Trp Asn Ser Glu
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 9

Pro Asp Gln Asp Ala Pro
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 10

Pro Asp Ser Trp His
 1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 11

Ser Lys Glu Leu
 1

<210> SEQ ID NO 12
```

```
<211> LENGTH: 4
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 12

Glu Ile Glu Phe
  1

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 13

Ser Arg Ser Gly His Ser
  1               5

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 14

Arg Phe Gln Glu Glu Ile Lys Glu Asn Thr Lys Asn Asp Lys Gln
  1               5                  10                  15

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 15

Thr Ser Tyr Pro Asp
  1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 16

Lys Glu Asn Thr Lys
  1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 17

Arg Tyr Gln Glu Glu
```

```
<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 18

Tyr Val Lys Gln Glu
 1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 19

Tyr Lys His Arg
 1

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 20

Tyr Cys Asp Arg Gly Trp Ala Cys Tyr
 1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 21

Tyr Cys Asp Gly Asp Leu Ala Thr Cys Tyr
 1               5                  10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 22

Tyr Cys Ser Asp Phe Ala Thr Glu Cys Tyr
 1               5                  10

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Novel
      Sequence
```

```
<400> SEQUENCE: 23

Tyr Cys Val Thr Lys Thr Ser Ile Lys Ile Pro Ser Ser His Cys Tyr
 1               5                  10                  15

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 24

Tyr Cys Lys Thr Ser Ile Lys Ile Pro Ser Ser His Cys Tyr
 1               5                  10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 25

Tyr Cys Tyr Trp Ser Asn Ser Glu Phe Cys Tyr
 1               5                  10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 26

Cys Tyr Trp Asn Ser Glu Cys Tyr
 1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 27

Tyr Cys Pro Asp Gln Asp Ala Pro Cys Tyr
 1               5                  10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 28

Tyr Cys Pro Asp Ser Trp His Cys Tyr Asp Glu
 1               5                  10

<210> SEQ ID NO 29
<211> LENGTH: 12
<212> TYPE: PRT
```

```
<213> ORGANISM: Artificial Sequence
<220> FEATURE:
<223> OTHER INFORMATION: Description of Artificial Sequence: Novel
      Sequence

<400> SEQUENCE: 29

Tyr Cys Ser Lys Glu Leu Cys Tyr Val Lys Gln Glu
 1               5                  10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 30

Tyr Cys Glu Ile Glu Phe Cys Tyr Lys His Arg
 1               5                  10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 31

Tyr Cys Ser Arg Ser Gly His Ser Cys Tyr
 1               5                  10

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 32

Tyr Cys Arg Phe Gln Glu Glu Ile Lys Glu Asn Thr Lys Asn Asp Lys
 1               5                  10                  15

Gln Cys Tyr

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 33

Tyr Cys Thr Ser Tyr Pro Asp Cys Ile
 1               5

<210> SEQ ID NO 34
<211> LENGTH: 15
<212> TYPE: PRT
```

```
<213> ORGANISM: Artificial Sequence
<220> FEATURE:
<223> OTHER INFORMATION: Description of Artificial Sequence: Novel
      Sequence

<400> SEQUENCE: 34

Arg Tyr Gln Glu Glu Cys Lys Glu Asn Thr Lys Cys Asp Lys Gln
 1               5                  10                  15
```

METHODS OF INHIBITING OSTEOCLAST ACTIVITY

This application is a divisional of U.S. patent application Ser. No. 10/625,073, filed Jul. 22, 2003, now allowed, which is a divisional of U.S. patent application Ser. No. 09/628,665, filed Jul. 28, 2000, now U.S. Pat. No. 6,673,771, which claims the benefit of U.S. Patent Application Ser. No. 60/146,094, filed Jul. 28, 1999, now expired. Each of the foregoing applications is incorporated herein by reference in its entirety for all purposes.

ACKNOWLEDGMENT OF GOVERNMENT RIGHTS

The present invention was made under Grant EY09332 from the National Institutes of Health. The Government may have certain rights to the invention.

FIELD OF THE INVENTION

The present invention relates to the methods of down-modulating osteoclastogenesis activity, thereby inhibiting bone matrix erosion and thus preventing bone loss and treating bone diseases.

BACKGROUND OF THE INVENTION

Osteoclasts are large multinuclear cells which function to erode bone matrix. They are related to macrophage and other cells that develop from monocyte cells. Like macrophage, osteoclasts are derived from haematopoietic progenitor cells.

Bone matrix erosion is a normal process which occurs in coordination with bone matrix formation, a process in which osteoblasts are involved. Essentially, osteoclasts erode bone matrix and tunnel into bone while osteoblasts follow, line the walls of the tunnel and form new bone matrix. Typically, in a normal adult, about 5-10% of bone is replaced by these processes annually.

Bone diseases such as osteoporosis and Paget's disease are characterized by a loss of bone. Similarly, metastatic bone disease, rheumatoid arthritis and peridontal bone disease are also characterized by bone loss. In many cases, bone loss leads to fractures in patients. In addition to the pain and suffering, patients become physically impaired which often leads to complications having negative consequences on patient health and quality of life. Moreover, the economic costs attributable to these diseases are tremendous.

Receptors and ligands of the Tumor Necrosis Factor family have recently been shown to play an essential part in the differentiation and activity of osteoclasts. On the one hand, Tumor Necrosis Factor-α (TNF-α) is known to promote osteoclastogenesis. On the other hand, a TNF-like molecule present on and/or secreted by osteoclasts and stromal cells, referred to interchangeably in the field and herein as Receptor activator of NF-κB ligand, (RANKL), Osteoclast differentiation factor (ODF), Osteoprotegerin ligand (OPGL), and TNF-related activation-induced cytokine (TRANCE), interacts with a TNF-receptor-like molecule, referred to in the field and herein as Receptor activator of NF-κB ligand, (RANK), which present in the membranes of osteoclast precursors and mature osteoclasts to regulate osteoclastogenesis and the resorbing activity of mature osteoclasts. The utilization of TNF-α antagonists, such as a monoclonal antibodies, for therapeutic purposes, has proven difficult, however, because of immunity to the large molecule, and limited entry into some specialized compartments of the body. Suda, et al. 1999 Endocrine Reviews 20(3):345-357, which is incorporated herein by reference, describes osteoclast differentiation and function. Filvaroff, E and R. Derynck 1998 Curr. Biol. 8:R679-R682, which is incorporated herein by reference, refer to bone remodeling and a signaling system for osteoclast regulation.

There is a need for methods of regulating osteoclastogenesis and the resorbing activity of mature osteoclasts. There is a need for methods of preventing bone loss and treating bone diseases.

SUMMARY OF THE INVENTION

The present invention relates to methods of inhibiting osteoclastogenesis and the resorbing activity of mature osteoclasts. According to the present invention, an amount of a TRANCE/RANK inhibitor effective to inhibit osteoclast bone erosion activity is administered to a patient.

The present invention relates to methods of treating patients who have diseases characterized bone loss. According to the present invention, an amount of a TRANCE/RANK inhibitor effective to inhibit osteoclastogenesis is administered to the patient.

The present invention relates to pharmaceutical compositions which comprise a TRANCE/RANK inhibitor in an amount effective to inhibit osteoclastogenesis.

The present invention relates to methods of modulating dendritic cell maturation, T cell proliferation, and/or CD40 receptor systems in an individual comprising the step of administering to the individual an amount of a TRANCE/RANK inhibitor effective to modulating dendritic cell maturation, T cell proliferation, and/or CD40 receptor systems.

The present invention relates to peptides that inhibit osteoclastogenesis, modulating dendritic cell maturation, T cell proliferation, and/or CD40 receptor systems

DETAILED DESCRIPTION OF PREFERRED EMBODIMENTS

As used herein, the term "TRANCE/RANK inhibitors" refers to the compounds which inhibit osteoclastogenesis and/or osteoclast function and which are described in PCT Application Serial Number PCT/US99/15062 filed Jul. 1, 1999 and entitled "CAVITY INDUCED ALLOSTERIC MODIFICATION OF INTERMOLECULAR INTERACTIONS AND METHODS OF IDENTIFYING COMPOUNDS THAT EFFECT THE SAME", which is incorporated herein by reference. TRANCE/RANK inhibitors can function as an antagonist of the cellular receptor RANK by inhibiting TRANCE/RANK. The Example below describes an assay which can be performed to identify peptides that inhibit osteoclastogensis and/or osteoclast function.

As used herein, the term "diseases characterized by bone loss" is meant to refer to diseases, conditions, disorders and syndromes which have as a symptom or pathology a decrease in bone mass or density. Examples of diseases characterized by bone loss include osteoporosis, Paget's disease, metastatic bone disease, rheumatoid arthritis and peridontal bone disease.

As used herein, the term "therapeutically effective amount" is meant to refer to an amount of a compound which produces a medicinal effect observed as reduction in the rate of bone loss in an individual when a therapeutically effective amount of a compound is administered to an individual who is susceptible to or suffering from a disease characterized by bone loss. Therapeutically effective amounts are typically determined by the effect they have compared to the effect observed when a composition which includes no active ingredient is administered to a similarly situated individual.

The invention provides methods for treating individuals that have diseases characterized by bone loss. TRANCE/RANK inhibitors are administered to the individual in an amount effective to inhibit osteoclastogenesis and/or osteoclast function and thereby reduce bone loss, i.e. a therapeutically effective amount.

The invention also provides novel therapeutic pharmaceutical compositions for treating diseases characterized by bone loss. The pharmaceutical compositions comprise a therapeutically effective amount of TRANCE/RANK inhibitors and a pharmaceutically acceptable carrier or diluent. In preferred embodiments, the pharmaceutical compositions are injectable pharmaceutical compositions, i.e. they are sterile, pyrogen-free, free of particulate matter, essentially isotonic with and otherwise suitable for injection into humans.

Applicants have discovered that the compounds and peptides described herein are useful to inhibit osteoclastogenesis and/or osteoclast function. By inhibiting osteoclastogenesis and/or osteoclast function, bone erosion can be prevented and bone loss can be reduced. Patients suffering from diseases characterized by bone loss can be treated by administering an amount of compounds effective to inhibit osteoclastogenesis and/or osteoclast function. In addition, patients identified as being susceptible to diseases characterized by bone loss can be prophylactically treated by administering an amount of compounds effective to inhibit osteoclastogenesis and/or osteoclast function.

Individuals who have a disease characterized by bone loss can be identified by those having ordinary skill in the art by well known diagnostic means and criteria. Individuals who are susceptible to a disease characterized by bone loss can be identified by those having ordinary skill in the art based upon family medical history and/or the presence of genetic markers or genes associated with a disease characterized by bone loss.

According to some embodiments of the invention, TRANCE/RANK inhibitors useful in the invention are compounds having Formula I which is set forth in the section below entitled Formulae. In compounds of Formula I, $R_1$ and $R_2$ are, independently, selected from the group consisting of —H, —OCH$_3$, —CH$_2$CH$_3$, -t-butyl, 3-carboxy-4-chlorophenylamino, —N—(CH$_2$CH$_2$OH)$_2$, and —O(O)C-Ph. $R_3$ is selected from the group consisting of —H, ethyl, —OCH$_3$, Cl, Br, F, 3-carboxy-4-chlorophenylamino, —N—(CH$_2$CH$_2$OH)$_2$, -t-butyl, and —OC(O)-Ph, and is not limited to attachment at any certain position on the phenyl ring to which it is attached. Preferably, $R_3$ is attached at either the 1 or 4 position of the phenyl ring. $R_4$ is selected from the group consisting of —Br, —Cl, and —F.

In some preferred compounds of Formula I:
  $R_1$, $R_2$, and $R_3$ are —OCH$_3$, $R_3$ is attached at the 4 position, and $R_4$ is —Cl;
  $R_1$ and $R_2$ are methyl, $R_3$ is ethyl, attached at the 4 position, and $R_4$ is —Cl;
  $R_1$ and $R_2$ are —OCH$_3$, $R_3$ is —Cl, attached at the 2 position, and $R_4$ is —Cl;
  $R_1$ and $R_2$ are —OCH$_3$ and $R_3$ is H, and $R_4$ is —Cl;
  $R_1$ is H, $R_2$ and $R_3$ are 3-carboxy-4-chlorophenylamino, and $R_3$ is attached at the 4 position, and $R_4$ is —Cl;
  $R_1$ and $R_2$ are —N(CH$_2$CH$_2$OH)$_2$, $R_3$ is Cl, attached at the 4 position, and $R_4$ is —Cl;
  $R_1$, $R_2$, and $R_3$ are t-butyl, $R_3$ is attached at the 4 position, and $R_4$ is —Cl;
  $R_1$ is —OCH$_3$, $R_2$ and $R_3$ are H, and $R_4$ is Cl; or
  $R_1$, $R_2$, and $R_3$ are benzoate, $R_3$ is attached at the 4 position, and $R_4$ is —Br.

Some preferred compounds of Formula I have the structures I-A, I-B, I-C, I-D, I-E, I-F, I-G, I-H or I-I which are set forth below in the section entitled Formulae.

These compounds are available from the following suppliers:

| Compound | Catalog Number | Supplier |
| --- | --- | --- |
| I-A | F36,700-1 | Aldrich, Milwaukee, WI |
| I-B | S11,245-3 | Aldrich, Milwaukee, WI |
| I-C | 00569 | Ryan Scientific, Isle of Palms, S.C. |
| I-D | F10,001-3 | Aldrich, Milwaukee, WI |
| I-E | 00129 | George UHE, Paramus, NJ |
| I-F | F37,166-1 | Aldrich, Milwaukee, WI |
| I-G | S-11,239-9 | Aldrich, Milwaukee, WI |
| I-H | F-27,721-5 | Aldrich, Milwaukee, WI |
| I-I | F12,920-8 | Aldrich, Milwaukee, WI |

In some embodiments, the TRANCE/RANK inhibitors are compounds having Formula II which is set forth below in the section entitled Formulae. In compounds having Formula II, $R_1$ is selected from the group consisting of -diphenylchloro methyl, -di(4-chlorophenyl)chloro methyl, and 4-(diphenylchloromethyl)phenyl; and $R_2$, $R_3$, $R_4$ are independently selected from the group consisting of —Br, —Cl, and —F, and are preferably —Cl.

Preferred compounds of Formula II have the structures II-A, II-B, II-C and II-D which are set forth below in the section entitled Formulae. These compounds are available from the following suppliers:

| Compound | Catalog Number | Supplier |
| --- | --- | --- |
| II-A | S5,479-9 | Aldrich, Milwaukee, WI |
| II-B | S5,755-0 | Aldrich, Milwaukee, WI |
| II-C | S5,740-2 | Aldrich, Milwaukee, WI |
| II-D | S5,751-8 | Aldrich, Milwaukee, WI |

According to some embodiments of the invention, TRANCE/RANK inhibitors useful in the invention are compounds having Formula III which is set forth in the section below entitled Formulae. In compounds of Formula III, R can be any of the following:

$R_1$=(NO$_2$), O(CO)CH$_3$, OH, O(CO)CH$_3$, O(CO)(CH$_2$)$_2$COOH, O(CO)CH$_2$Br, O(CO)CH$_2$Cl, O(CO)CH$_2$N(CH$_3$)$_3$, or OC$_5$H$_9$O;

$R_2$=CH$_2$O(NO$_2$), CHO, CH$_2$O(NO$_2$), CN, CH$_3$, COOH, CHNOH, CH$_2$O(CO)(CH$_2$)$_2$COOH, CHN(NH)CONH$_2$, CHN(NH)C$_6$H$_5$, CHN(CH$_2$)C$_6$H$_5$, CH$_2$N(CH$_2$)$_2$OH, CH$_2$NC$_6$H$_5$, or CH$_2$N(NH)CSNH$_2$;

$R_3$=OH, or H;

$R_4$=CH$_3$;

$R_5$=OH;

$R_6$=C$_4$H$_3$O$_2$, N(NHCO)C$_6$H$_4$Cl, N(NHCO)C$_6$H$_4$F, COOH, O, COCH$_3$, CH(CH$_3$)(CH$_2$)$_2$COOH, CH(CH$_3$)(CH$_2$)$_2$COOCH$_3$, O(CO)C$_6$H$_5$, or OH;

$R_7$=O(CO)CH$_2$N(CH$_3$)$_3$, or O(CO)CH$_3$;

$R_8$=OH;

$R_9$=O, or OH;

$R_{10}$=O.

Some preferred compounds of Formula III have the structures III-1 through III-31 which are set forth below in the section entitled Formulae and are described in the table below which includes catalogue numbers from ChemDiv, Inc., San Diego, Calif.

| Number | Catalogue # | Formula |
|---|---|---|
| III-1 | 0449-0070 | R1 = O(NO$_2$); R2 = CH$_2$O(NO$_2$); R3 = R5 = OH; R4 = CH$_3$; R6 = C$_4$H$_3$O$_2$ |
| III-2 | 0449-0037 | R1 = R3 = R5 = R8 = OH; R2 = CHO; R4 = CH$_3$; R6 = C$_4$H$_3$O$_2$ |
| III-3 | 0449-0071 | R1 = R3 = R5 = OH; R2 = CH$_2$O(NO2); R6 = C$_4$H$_3$O$_2$ |
| III-4 | 0449-0077 | R1 = O(CO)CH$_3$; R2 = CN; R3 = R5 = OH; R4 = CH$_3$; R6 = C$_4$H$_3$O$_2$ |
| III-5 | 0449-0095 | R1 = R3 = R5 = OH; R2 = R4 = CH$_3$; R6 = C$_4$H$_3$O$_2$ |
| III-6 | 0449-0101 | R1 = R3 = R5 = OH; R2 = COOH; R4 = CH$_3$; R6 = C$_4$H$_3$O$_2$ |
| III-7 | 0449-0112 | R1 = O(CO)CH3; R2 = CHO; R3 = R5 = OH; R4 = CH$_3$; R6 = C$_4$H$_3$O$_2$ |
| III-8 | 0449-0113 | R1 = O(CO)CH3; R2 = R4 = CH3; R3 = H; R5 = OH; R6 = C$_4$H$_3$O$_2$ |
| III-9 | 0449-0115 | R1 = O(CO)(CH$_2$)$_2$COOH; R2 = CHO; R3 = R5 = OH; R4 = CH$_3$; R6 = C$_4$H$_3$O$_2$ |
| III-10 | 0449-0116 | R1 = R3 = R5 = OH; R2 = CHNOH; R4 = CH$_3$; R6 = C$_4$H$_3$O$_2$ |
| III-11 | 0449-0119 | R1 = O(CO)(CH$_2$)$_2$COOH; R2 = CH$_2$O(CO)(CH$_2$)$_2$COOH; R3 = R5 = OH; R4 = CH$_3$; R6 = C$_4$H$_3$O$_2$ |
| III-12 | 0449-0120 | R1 = O(CO)CH$_2$Br; R2 = CH$_3$; R3 = H; R4 = CH$_3$; R5 = OH; R6 = C$_4$H$_3$O$_2$ |
| III-13 | 0449-0160 | R1 = O(CO)CH$_2$Cl; R2 = CHO; R3 = R5 = OH; R4 = CH$_3$; R6 = C$_4$H$_3$O$_2$ |
| III-14 | 0449-0719 | R1 = OH; R2 = R4 = CH$_3$; R6 = N(NHCO)C$_6$H$_4$Cl |
| III-15 | 0449-0720 | R1 = OH; R2 = R4 = CH$_3$; R6 = N(NHCO)C$_6$H$_4$F |
| III-16 | N001-0005 | R1 = R5 = OH; R2 = CHO; R3 = H; R4 = CH$_3$; R6 = C$_4$H$_3$O$_2$ |
| III-17 | N008-0012 | R1 = O(CO)CH$_2$N(CH$_3$)$_3$; R2 = R4 = CH$_3$; R5 = OH; R6 = C$_4$H$_3$O$_2$; R7 = O(CO)CH$_2$N(CH$_3$)$_3$ |
| III-18 | N023-0001 | R1 = OH; R2 = R4 = CH$_3$; R3 = R5 = OH; R6 = C$_4$H$_3$O$_2$; R7 = O(CO)CH$_3$ |
| III-19 | N023-0004 | R1 = OH; R2 = CHN(NH)CONH$_2$; R3 = R5 = OH; R4 = CH$_3$; R6 = C$_4$H$_3$O$_2$ |
| III-20 | N023-0005 | R1 = R3 = R5 = OH; R2 = CHN(NH)C$_6$H$_5$; R4 = CH3; R6 = C$_4$H$_3$O$_2$ |
| III-21 | N023-0006 | R1 = R3 = R5 = OH; R2 = CHN(CH$_2$)C$_6$H$_5$; R4 = CH3; R6 = C$_4$H$_3$O$_2$ |
| III-22 | N023-0007 | R1 = OH; R2 = CH$_2$N(CH$_2$)$_2$OH; R4 = CH$_3$; R3 = R5 = OH; R6 = C$_4$H$_3$O$_2$ |
| III-23 | N023-0008 | R1 = OH; R2 = CH$_2$NC$_6$H$_5$; R3 = R5 = OH; R4 = CH$_3$; R6 = C$_4$H$_3$O$_2$ |
| III-24 | N023-0025 | R1 = OH; R2 = CH$_2$N(NH)CSNH$_2$; R3 = R5 = OH; R4 = CH$_3$; R6 = C$_4$H$_3$O$_2$ |
| III-25 | N039-0025 | R1 = OH; R2 = R4 = CH$_3$; R3 = H; R6 = COCH$_3$ |
| III-26 | S003-0002 | R1 = OH; R2 = R4 = CH$_3$; R3 = H; R6 = COOH |
| III-27 | S003-0006 | R1 = OH; R2 = R4 = CH$_3$; R3 = H; R6 = CH(CH$_3$)(CH$_2$)$_2$COOH; R9 = O |
| III-28 | S003-0007 | R1 = OH; R2 = R4 = CH$_3$; R3 = H; R6 = CH(CH$_3$)(CH$_2$)2COOCH$_3$; R9 = OH; R10 = O |
| III-29 | S003-0009 | R2 = R4 = CH$_3$; R3 = H; R6 = O |
| III-30 | S003-0014 | R1 = OH; R2 = R4 = CH$_3$; R3 = H; R6 = O(CO)C$_6$H$_5$ |
| III-31 | S003-0012 | R1 = O(C$_5$H$_9$O); R2 = R4 = CH$_3$; R3 = H; R6 = OH |

According to some embodiments of the invention, TRANCE/RANK inhibitors useful in the invention are compounds having Formula IV which is set forth in the section below entitled Formulae. In compounds of Formula IV, R can be any of the following:

$R_1$=O(CO)(CH$_2$)$_2$COOH, or O(CO)CH$_2$Br;
$R_2$=O(CO)(CH$_2$)$_2$COOH, or O(CO)CH$_2$Br.

Some preferred compounds of Formula IV have the structures IV-1 through IV-2 which are set forth below in the section entitled Formulae and are described in the table below which includes catalogue numbers from ChemDiv, Inc., San Diego, Calif.

| Number | Catalogue # | Formula |
|---|---|---|
| IV-1 | 0521-0013 | R1 = R2 = O(CO)(CH$_2$)$_2$COOH |
| IV-2 | 0521-0014 | R1 = R2 = O(CO)CH$_2$Br |

According to some embodiments of the invention, TRANCE/RANK inhibitors useful in the invention are compounds having Formula V which is set forth in the section below entitled Formulae. In compounds of Formula V, R can be any of the following:

$R_1$=O, OH, or O(CO)CH$_3$
$R_2$=O(CO)CH$_3$, OH, CO(CH$_3$), or CO(CH$_2$)O(CO)CH$_3$,
$R_3$=CH$_3$, or OH
$R_4$=O(CO)CH$_2$C$_6$H$_4$I, or CH$_3$

Some preferred compounds of Formula V have the structures V-1 through V-5 which are set forth below in the section entitled Formulae and are described in the table below which includes catalogue numbers from ChemDiv, Inc., San Diego, Calif.

| Number | Catalogue # | Formula |
|---|---|---|
| V-1 | N017-0002 | R1 = O; R2 = O(CO)CH$_3$; R3 = CH$_3$ |
| V-2 | N017-0003 | R1 = OH; R2 = OH; R3 = CH$_3$ |
| V-3 | N017-0005 | R1 = O(CO)CH$_3$; R2 = CO(CH$_3$); R3 = OH; R4 = O(CO)CH$_2$C$_6$H$_4$I |
| V-4 | N017-0006 | R1 = O; R2 = CO(CH$_2$)O(CO)CH$_3$; R3 = OH |
| V-5 | N017-0012 | R1 = OH; R2 = CO(CH$_3$); R3 = OH; R4 = CH$_3$ |

According to some embodiments of the invention, TRANCE/RANK inhibitors useful in the invention are compounds having Formula VI which is set forth in the section below entitled Formulae. In compounds of Formula VI, R can be any of the following:

$R_1$=O(CO)CH$_3$, OH, or O(CO)(CH$_2$)$_2$COOH
$R_2$=CH$_3$
$R_3$=O, or OH
$R_4$=CH$_3$;
$R_5$=C$_9$H$_{13}$COCH$_3$, C$_9$H$_{13}$(CH$_2$CH$_3$)(CH$_2$OH), C$_9$H$_{13}$(CH$_2$CH$_3$)(CH$_2$OCOCH$_3$), C$_9$H$_{13}$(CH$_2$CH$_3$)(CH$_2$OCO(CH$_2$)$_2$COOH), C$_9$H$_{13}$(CH$_2$CH$_3$)(COOH), or C$_8$H$_7$O(CH$_3$)(C$_4$H$_9$OCH$_3$)
$R_6$=CH$_3$
$R_7$=O, or H
$R_8$=CH$_3$
$R_9$=(CH$_3$)$_2$
$R_{10}$=Br.

Some preferred compounds of Formula V have the structures VI-1 through VI-11 which are set forth below in the section entitled Formulae and are described in the table below which includes catalogue numbers from ChemDiv, Inc., San Diego, Calif.

| Number | Catalogue # | Formula |
|---|---|---|
| VI-1 | N017-0018 | R1 = O(CO)CH$_3$; R2 = CH$_3$; R3 = O; R7 = H; R4 = CH$_3$; R5 = C9H$_{13}$COCH$_3$ |
| VI-2 | N017-0019 | R1 = OH; R2 = R4 = CH$_3$; R3 = OH; R5 = C$_9$H$_{13}$COCH$_3$ |
| VI-3 | N032-0001 | R1 = OH; R9 = (CH$_3$)$_2$; R2 = R6 = R8 = CH$_3$; R5 = C$_9$H$_{13}$(CH$_2$CH$_3$)(CH$_2$OH) |
| VI-4 | N032-0002 | R1 = O(CO)CH3; R9 = (CH$_3$)$_2$; R2 = R6 = R8 = CH$_3$; R5 = C$_9$H$_{13}$(CH$_2$CH$_3$)(CH$_2$OH) |
| VI-5 | N032-0003 | R1 = OH; R9 = (CH$_3$)$_2$; R2 = R6 = R8 = CH$_3$; R5 = C$_9$H$_{13}$(CH$_2$CH$_3$)(CH$_2$O(CO)CH$_3$) |
| VI-6 | N032-0004 | R1 = O(CO)(CH$_2$)$_2$COOH; R9 = (CH$_3$)$_2$; R2 = R6 = R8 = CH$_3$; R5 = C$_9$H$_{13}$(CH$_2$CH$_3$)CH$_2$O(CO)(CH$_2$)$_2$COOH |
| VI-7 | N032-0006 | R1 = O; R2 = R6 = R8 = CH$_3$; R5 = C$_9$H$_{13}$(CH$_2$CH$_3$)(COOH); R9 = (CH$_3$)$_2$ |
| VI-8 | N039-0023 | R1 = O(CO)CH$_3$; R2 = R4 = CH$_3$; R5 = C$_8$H$_7$O(CH$_3$)C$_4$H$_9$OCH$_3$) |
| VI-9 | N039-0029 | R1 = OCOCH$_3$; R2 = R4 = CH$_3$; R3 = OH; R7 = O; R10 = Br; R5 = C$_8$H$_7$O(CH$_3$)C$_4$H$_9$OCH$_3$) |
| VI-10 | N039-0031 | R1 = OH; R2 = R4 = CH3; R3 = OH; R7 = O; R5 = C$_8$H$_7$O(CH$_3$)C$_4$H$_9$OCH$_3$) |
| VI-11 | N039-0032 | R1 = OH; R2 = R4 = CH3; R7 = OH; R5 = C$_8$H$_7$O(CH$_3$)C$_4$H$_9$OCH$_3$) |

According to some embodiments of the invention, TRANCE/RANK inhibitors useful in the invention are compounds have structures of Formulae VII to XII set forth in the section below entitled Formulae. Compounds of Formulae VIII to XII and are described in the table below which includes catalogue numbers from ChemDiv, Inc., San Diego, Calif.

| Number | Catalogue # |
|---|---|
| VII | 0836-0110 |
| VIII | N002-0041 |
| IX | N039-0046 |
| X | S003-0004 |
| XI | S003-0018 |
| XII | N001-0001 |

According to the invention, TRANCE/RANK inhibitors useful in the invention to treat diseases characterized by bone loss may be formulated and administered as follows. The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hank's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

The compounds of the invention will generally be used in an amount effective to achieve the intended purpose. For use to treat or prevent TNF-associated disorders, the compounds of the invention, or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that inhibits 50% of TRANCE/RANK-binding interactions). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day. Some preferred dosages range from 1 nM to 500 mM. Some preferred dosages range from 1 mM to 500 mM. Some preferred dosages range from 1 mg to 500 mg. Some preferred dosages range from 1000 mg to 3000 mg. Some preferred dosages range from 1500 mg to 2500 mg. According to the invention, TRANCE/RANK inhibitors are administered one to four times per day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use human. The dosage of the compounds described lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p. 1). Preferred dosages range from 1 nM to 500 mM.

Pharmaceutical compositions according to the present invention comprise TRANCE/RANK inhibitors formulated as described above in therapeutically effective doses. In some embodiments, the pharmaceutical compositions is sterile and pyrogen free.

Other aspects of the present invention include the use of TRANCE/RANK inhibitors in methods involving other cell types in which TRANCE/RANK mediated signaling is involved in cell development and/or activity. Such cell types include antigen presenting cells such as dendritic cells and lymphocytes. Anderson et al. 1997 Nature 390:175-179, refer to the RANK/RANKL in T cells and dendritic cells. Similarly, Kong et al. 1999 Immunol. and Cell Biology 77:188-193 refer to osteoprotegerin ligand as a common link between osteoclastogenesis, lymphnode formation and lymphocyte development. In addition, Wong et al. 1999 J. Leukocyte Biology 65:715-724 refer to TRANCE as regulating dendritic cell and osteoclast function. TRANCE/RANK inhibitors formulated as described above in effective doses can be used to modulate dendritic cell maturation and function, T cell proliferation and CD40 receptor systems.

According to some aspects of the invention, the present invention relates to novel peptides and methods using such novel peptides.

The aromatically modified peptides of the invention comprise an amino acid sequence that consists of 27 amino acid residues and has the formula:

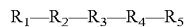

wherein:
R$_1$ is 1-5 amino acid residues;
R$_2$ is a linking amino acid residue;
R$_3$ is selected from the group consisting of: DRGWA (SEQ ID NO:1); DGDLAT (SEQ ID NO:2); SDFATE (SEQ ID NO:3); VTKTSIKIPSSH (SEQ ID NO:4); TKTSIKIPSSH (SEQ ID NO:5); KTSIKIPSSH (SEQ ID NO:6); YWSNSEF (SEQ ID NO:7); YWNSE (SEQ ID NO:8); PDQDAP (SEQ ID NO:9); PDSWH (SEQ ID NO:10); SKEL (SEQ ID NO:11); EIEF (SEQ ID NO:12); SRSGHS (SEQ ID NO:13); RFQEEIKENTKNDKQ (SEQ ID NO:14); TSYPD (SEQ ID NO:15); KENTK (SEQ ID NO:16); and conservatively substituted derivatives thereof;
R$_4$ is a linking amino acid residue;
R$_5$ is 1-5 amino acid residues; and
wherein R$_2$ and R$_4$ are bound to each other, thereby forming a cyclic portion which includes R$_2$, R$_3$ and R$_4$ with R$_1$ and R$_5$ forming exocyclic portions, and one or both of R$_1$ and R$_5$ comprising at least one tyrosine or phenylalanine.

The aromatically modified peptides of the invention comprise an amino acid sequence that consists of 27 amino acid residues and has the formula:

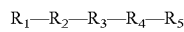

wherein:
R$_1$ is 1-5 amino acid residues including at least one tyrosine or phenylalanine;
R$_2$ is cysteine;
R$_3$ is selected from the group consisting of: DRGWA (SEQ ID NO:1); DGDLAT (SEQ ID NO:2); SDFATE (SEQ ID NO:3); VTKTSIKIPSSH (SEQ ID NO:4); TKTSIKIPSSH (SEQ ID NO:5); KTSIKIPSSH (SEQ ID NO:6); YWSNSEF (SEQ ID NO:7); YWNSE (SEQ ID NO:8); PDQDAP (SEQ ID NO:9); PDSWH (SEQ ID NO: 10); SKEL (SEQ ID NO:11); EIEF (SEQ ID NO:12); SRSGHS (SEQ ID NO:13); RFQEEIKENTKNDKQ (SEQ ID NO:14); TSYPD (SEQ ID NO:15); KENTK (SEQ ID NO:16); and conservatively substituted derivatives thereof;
R$_4$ is cysteine;
R$_5$ is 1-5 amino acid residues including at least one tyrosine or phenylalanine; and
wherein R$_2$ and R$_4$ are bound to each other, thereby forming a cyclic portion which includes R$_2$, R$_3$ and R$_4$ with R$_1$ and R$_5$ forming exocyclic portions.

The aromatically modified peptides of the invention comprise an amino acid sequence that consists of 27 amino acid residues and has the formula:

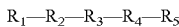

wherein:
R$_1$ is selected from the group consisting of: absent, Y; RYQEE (SEQ ID NO:17); and conservatively substituted derivatives thereof;
R$_2$ is cysteine;
R$_3$ is selected from the group consisting of: DRGWA (SEQ ID NO:1); DGDLAT (SEQ ID NO:2); SDFATE (SEQ ID NO:3); VTKTSIKIPSSH (SEQ ID NO:4); TKTSIKIPSSH (SEQ ID NO:5); KTSIKIPSSH (SEQ ID NO:6); YWSNSEF (SEQ ID NO:7); YWNSE (SEQ ID NO:8); PDQDAP (SEQ ID NO:9); PDSWH (SEQ ID NO:10); SKEL (SEQ ID NO:11); EIEF (SEQ ID NO:12); SRSGHS (SEQ ID NO:13); RFQEEIKENTKNDKQ (SEQ ID NO:14); TSYPD (SEQ ID NO:15); KENTK (SEQ ID NO:16); and conservatively substituted derivatives thereof;
R$_4$ is cysteine;
R$_5$ is selected from the group consisting of Y; Y—[NH2]; YDE; YDE-[NH2]; YVKQE (SEQ ID NO:18); YVKQE-[NH2]; YKHR (SEQ ID NO:19); YKHR—[NH2]; I; I—[NH2]; DKQ and CDKQ-[NH2] and conservatively substituted derivatives thereof; and wherein R$_2$ and R$_4$ are bound to each other, thereby forming a cyclic portion which includes R$_2$, R$_3$ and R$_4$ with R$_1$ and R$_5$ forming exocyclic portions, and one or both of R$_1$ and R$_5$ comprising at least one tyrosine or phenylalanine.

In preferred embodiments, the peptide is selected from the group consisting of: YCDRGWACY (SEQ ID NO:20); YCDGDLATCY (SEQ ID NO:21); YCSDFATECY (SEQ ID NO:22); YCVTKTSIKIPSSHCY (SEQ ID NO:23); YCKTSIKIPSSHCY (SEQ ID NO:24); YCYWSNSEFCY (SEQ ID NO:25); CYWNSECY (SEQ ID NO:26); YCPDQDAPCY (SEQ ID NO:27); YCPDSWHCYDE (SEQ ID NO:28); YCSKELCYVKQE (SEQ ID NO:29); YCEIEFCYKHR (SEQ ID NO:30); YCSRSGHSCY (SEQ ID NO:31); YCRFQEEIKENTKNDKQCY (SEQ ID NO:32); YCTSYPDCI (SEQ ID NO:33); RYQEECKENTKCDKQ (SEQ ID NO:34); and conservatively substituted derivatives thereof.

Preferred peptides according to the invention are:

```
SEQ ID NOs: 20-30 with amidated C termini
RL 1-1:  [H]-YC DRGWA CY-[NH2]
RL 2-1:  [H]-YC DGDLAT CY-[NH2]
RL 2-2:  [H]-YC SDFATE CY-[NH2]
RL 3-1:  [H]-YC VTKTSIKIPSSH CY-[NH2]
RL 3-2:  [H]-YC KTSIKIPSSH CY-[NH2]
RL 4-1:  [H]-YC YWSNSEF CY-[NH2]
RL 4-2:  [H]-C YWNSE CY-[NH2]
RL 5-1:  [H]-YC PDQDAP CY-[NH2]
OP 1:    [H]-YC PDSWH CYDE-[NH2]
OP 2:    [H]-YC SKEL CYVKQE-[NH2]
OP 3:    [H]-YC EIEF CYKHR-[NH2]
and SEQ ID NO: S 31-34
TR-LSS  YC SRSGHS CY
TR-LRQ  YC RFQEEIKENTKNDKQ CY
TR-LTI  YC TSYPD CI
TR-LED  RYQEEC KENTK CDKQ.
```

Generally, a compound of the present invention is a cyclic peptide or peptide analogue which is modified at its termini with hydrophobic moieties. In certain embodiments, one or more amino acid residues within the peptide are substituted with other amino acid residues. Typically, such amino acid substitutions are conservative, i.e., the amino acid residues are replaced with other amino acid residues having similar physical and/or chemical properties. In embodiments wherein the compound is a peptide analogues, the analogues is obtained by replacing at least one amide linkage in the peptide with a substituted amide or an isostere of amide.

"Aromatic moiety:" refers to a moiety having an unsaturated cyclic hydrocarbon group which has a conjugated $(4n=2)\pi$ electron system. typical aromatic moieties include, but are not limited to, benzene, naphthalene, anthracene, azulene, indacene, and the like. In preferred embodiments, the aromatic moiety contains 5-20 carbons in the ring system, with 5-10 carbon atoms being particularly preferred.

"Substituted Aromatic Moiety:" refers to an aromatic moiety wherein one or more hydrogen atoms are each independently replaced with other substituents.

"Heteroaromatic moiety:" refers to an aromatic moiety wherein one or more of the ring carbon atoms is replaced with another atom such as N, O or S. Typical heteroaromatic moieties include, but are not limited to, pyran, pyrazole, pyridine, pyrrolke, pyrazine, pyridazine, pyrimidine, pyrrolizine, quinazoline, quinoline, quinolizine, quinoxaline, selenophene, thiophere, tellurophene, xanthene and the like.

"Substituted Heteroaromatic moiety:" refers to a heteroaromatic moiety wherein one or more hydrogen atoms are each independently replaced with other substituents.

Generally, a compound of the present invention is a cyclic peptide or peptide analogue. The peptide or peptide analogue is modified at its termini with hydrophobic moieties. In certain embodiments, one or more amino acid residues within the peptide are substituted with other amino acid residues. Typically, such amino acid substitutions are conservative, i.e., the amino acid residues are replaced with other amino acid residues having physical and/or chemical properties similar to the residues they are replacing. Preferably, conservative amino acid substitutions are those wherein an amino acid is replaced with another amino acid encompassed within the same designated class, as will be described more thoroughly below. In embodiments wherein the compound is a peptide analogue, the analogue is obtained by replacing at least one amide linkage in the peptide with a substituted amide or an isostere of amide.

The amino acid residues may be the genetically encoded L-amino acids, naturally occurring non-genetically encoded L-amino acids, synthetic L-amino acids or D-enantiomers of all of the above. The amino acid notations used herein for the twenty genetically encoded L-amino acids and common non-encoded amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-alanine | | bAla |
| 2,3-diaminopropionic acid | | Dpr |
| -α-aminoisobutyric acid | | Aib |
| N-Methylglycine (sarcosine) | | MeGly |
| Ornithine | | Orn |
| Citrulline | | Cit |
| t-buytlalanine | | t-BuA |
| t-butylglycine | | t-Bug |
| N-methylisoleucine | | MeIle |
| phenylglycine | | Phg |
| cyclohexylalanine | | Cha |
| Norleucine | | Nle |
| naphthylalanine | | Nal |
| Pyridylananine | | |
| 3-benzothienyl alanine | | |
| 4-chlorophenylalanine | | Phe(4-Cl) |
| 2-fluorophenylalanine | | Phe(2-F) |
| 3-fluorophenylalanine | | Phe(3-F) |
| 4-fluorophenylalanine | | 9 |
| Penicillamine | | Pen |
| 1,2,3,4-tetrahydroisoquinoline-3-carboxylic acid | | Tic |
| β-thienylalanine | | Thi |
| Methionine sulfoxide | | MSO |
| Homoarginine | | hArg |
| N-acetyl lysine | | AcLya |
| 2,4-diamino butyric acid | | Dbu |
| p-aminophenylalanine | | Phe(pHN$_2$) |
| N-methylvaline | | MeVal |
| Homocysteine | | hCys |
| Homoserine | | hSer |
| ε-amino hexanoic acid | | Aha |

The compounds that are encompassed within the scope of the invention are partially defined in terms of amino acid residues of designated classes. The amino acids may be generally categorized into three main classes: hydrophilic amino acids, hydrophobic amino acids and Cysteine-like amino acids, depending primarily on the characteristics of the amino acid side chain. These amino classes may be further divided into subclasses. Hydrophilic amino acids include amino acids having acidic, basic or polar side chains and hydrophobic amino acids including amino acids having aromatic or apolar side chains. Apolar amino acids ma be further subdivided to include, among others, aliphatic amino acids. The definitions of the classes of amino acids as used herein are as follows:

Hydrophobic Amino Acid refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

Aromatic Amino Acid refers to a hydrophobic amino acid having a side chain containing at least one ring having a conjugated π-electron system (aromatic group). The aromatic group may be further substituted with substituent groups such as alkyl, alkenyl, alkynyl, hydroxyl, sulfanyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chloro-phenylalanine, 2-fluorophenylalanine, 3-fluorophenylalanine and 4-fluorophyenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2.4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-encoded cysteine-like amino acids include homocysteine and penicillamine.

As will be appreciated by those having skill in the art, the above classification are not absolute—several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids which are not genetically encoded of which the peptides and peptide analogues of the invention may be composed include, but are not limited to, β-alanine (B-Ala) and other omega-amino acids such as 3-aminopropionic acid (Dap), 2.3-diaminopropionic acid (Dpr), 4-aminobutyric acid and so forth; α-aminoisobutyric acid (Aib); ε-aminohyxanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (phg); cyclohexylalanine (Cha); norleucine (Nle); 2-naphythylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MOS); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall conveniently into the categories defined above.

The classifications of the above-described genetically encoded and non-encoded amino acids are summarized in Table 1, below. It is to be understood that Table 1 is for illustrative purposes only and does not purport to be an exhaustive list of amino acid residues which may comprise the peptides and peptide analogues described herein. Other amino acid residues which are useful for making the peptides and peptide analogues described herein can be found, e.g., in Fasman, 1989, *CRC* Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 1

| Classification | Genetically Encoded | Genetically Non-Encoded |
| --- | --- | --- |
| Hydrophobic | | |
| Aromatic | F, Y, W | Phg, Nal, Thi, Tic, Phe(4-Cl), Phe(2-F), Phe(3-F), Phe(4-F); Pyridyl Ala, Benzothienyl Ala |
| Apolar | M, G, P | |
| Aliphatic | A, V, L, I | T-BuA, T-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$BU |
| Polar | Q, N, S, T, Y | Cit, AcLys, MSO, hSer |
| Cysteine-Like | C | Pen, hCys, β-methyl Cys |

A linking amino acid residue is one forming covalent linkages with another so as to allow cyclization of the peptide. Examples of amino acid residues which are capable of forming covalent linkages with one another include cysteine-like amino acids such as Cys, hCys, β-methyl Cys and Pen, which are capable of forming disulfide bridges with one another. Preferred cysteine-like amino acid residues include Cys and Pen.

Amino acids used to cyclize a peptide need not be cysteine-like amino acids. Pairs of amino acids that have side chain functional groups capable of forming covalent linkages with one another can also be used. Such pairs of functional groups are known to those of skill in the art and include, inter alia, —COOH and —OH, —COOH and —NH$_2$, and —COOH and —SH. Thus, pairs of amino acids that can be used to cyclize a peptide include, inter alia, Asp and Lys; Glu and Lys; Asp and Arg; Glu and Arg; Asp and Ser; Glu and Ser; Asp and Thr; Glu and Thr; Asp and Cus; and Glu8 and Cys. Other pairs of amino acids which can be used to cyclize the peptide will be apparent to those skilled in the art.

Equivalents of linking amino acids include groups used to cyclize a peptide such as any molecule having three functional groups—one functional group capable of forming a covalent linkage with a terminus of the peptide, a second functional group capable of forming a covalent linkage with the second functional group of another group, and a third functional group capable of forming a covalent linkage with hydrophobic moieties. Molecules having a suitable functional groups will be apparent to those skilled in the art. Examples of functional groups capable of forming a covalent linkage with the amino terminus of a peptide include carboxylic acids and esters. Examples of functional groups capable of forming a covalent linkage with the carboxyl terminus of a peptide include —OH, —SH, —NH$_2$ and —NHR where R is ($C_1$-$C_6$) alkyl, ($C_1$-$C_6$) alkenyl and ($C_1$-$C_6$) alkynyl.

A variety of interlinkages useful to cyclize a peptide can be generated by reaction between two functional groups suitable for forming such interlinkages, as well as reaction conditions suitable for forming such interlinkages, will be apparent to those of skill in the art. Preferably, the reaction conditions used to cyclize the peptides are sufficiently mild so as not to degrade or otherwise damage the peptide. Suitable groups for protecting the various functionalities as necessary are well know in the art (see, e.g., Green & Wuts, 1991, $2^{nd}$ ed., John Wiley & Sons NY), as are various reaction schemes for preparing such protected molecules.

The exocylic portions of the peptides represent a hydrophobic moiety. While not intending to be bound by any particular theory, it is believed that when placed in aqueous solution, these hydrophobic moieties interact so as to confer the peptide with structural stability. A significant hydrophobic interaction for conferring structural stability is thought to be stacking of aromatic rings. Thus, in a preferred embodiment, $R_1$ and $R_5$ designate 1-5 amino acids, at least one of which is an aromatic amino acid or an aromatic or heteroaromatic moiety. More preferably, each of $R_1$ and $R_5$ include an aromatic amino acid or an aromatic or heteroaromatic moiety. Suitable aromatic amino acids include Tyr and Phe being preferred. Suitable aromatic or heteroaromatic moieties include phenyl, naphthyl, purine, pyrimidine, and the like.

In the peptides having the formula $R_1$—$R_2$—$R_3$—$R_4$—$R_5$, the symbol "—" between amino acid residues generally designates a backbone interlinkage. Thus, the symbol "—" usually designates an amide linkage (—C(O)—NH). It is to be understood, however, that in all of the peptides described in the specific embodiments herein, one or more amide linkages may optionally be replaced with a linkage other than amide, preferably a substituted amide or an isostere of an amide linkage. Thus, while the various R groups have generally been described in terms of amino acids, one having skill in the art will recognize that in embodiments having non-amide linkages, the term "amino acid" refers to other bifunctional moieties having side-chain groups similar to the side chains of the amino acids. For example, in embodiments having non-amide linkages, the phrase "acidic amino acid" refers to a bifunctional molecule capable of forming the desired backbone interlinkages and which has a side chain group similar to the side chain of an acidic amino acid. Substituted amides generally include groups of the formula —C(O)—NR, where R is ($C_1$-$C_6$) alkyl, ($C_1$-$C_6$) alkenyl, ($C_1$-$C_6$) alkynyl, substituted ($C_1$-$C_6$) alkyl, substituted ($C_1$-$C_6$) alkenyl or substituted ($C_1$-$C_6$) alkynyl. Isosteres of amide generally include, but are not limited to, —$CH_2NH$—, —$CH_2S$—, —$CH_2CH_2$—, —CH=CH— (cis and trans), —C(O)$CH_2$— and —$CH_2S$—.

Compounds having such linkages and methods for preparing such compounds are well-known in the art (see, e.g., Spatola, 1983, Vega Data 1(3) for a general review); Spatola, 1983, "Peptide Backbone Modifications" In: Chemistry and Biochemistry of Amino Acids Peptides and Proteins (Weinstein, ed.), Marcel Dekker, New York, p. 267 (general review); Morley, 1980, Trends Pharm. Sci. 1:463-468; Hudson et al., 1979, Int. J. Prot. Res. 14:177-185 (—$CH_2NH$—, —$CH_2CH_2$—); Spatola et al., 1986, *Life Sci.* 38:1243-1249 (—$CH_2$—S); Hann, 1982, J. Chem. Soc. Perkin Trans. I. 1:307-314 (—CH=CH—, cis and trans); Jennings-White et al., Tetrahedron. Lett. 23:1392-1398 (—COCH$_2$—); European Patent Application EP 45665 (1982) CA:97:39405 (—CH(OH)CH$_2$—); Holladay et al., 1983, Tetrahedron Lett. 24:4401-4404 (—C(OH)CH$_2$—); and Hruby, 1982, Life Sci. 31:189-199 (—CH$_2$—S—).

In all of the aforementioned embodiments of the invention, it is to be understood that the phrase "amino acid" also refers to bifunctional moieties having amino acid-like side chains, as previously described.

Generally, active peptides or peptide analogues of the invention are those that exhibit at least about 15% inhibition in the Trap assay set forth in the example. Preferably, active peptides of the invention or analogues thereof will exhibit at least about 20% to 50% or even 80% or more inhibition.

The peptides of the invention or analogues thereof, may be prepared using virtually any art-known technique for the preparation of peptides and peptide analogues. For example, the peptides may be prepared in linear or non-cyclized form using conventional solution or solid phase peptide syntheses and cyclized using standard chemistries. Preferably, the chemistry used to cyclize the peptide will be sufficiently mild so as to avoid substantially degrading the peptide. Suitable procedures for synthesizing the peptides described herein as well as suitable chemistries for cyclizing the peptides are well known in the art.

Formation of disulfide linkages, if desired, is generally conducted in the presence of mild oxidizing agents. Chemical, enzymatic or photolytic oxidation agents may be used. Various methods are known in the art, including those described, for example, by Tam, J. P. et al., 1979, Synthesis 955-957; Stewart et al., 1984, Solid Phase Peptide Synthesis. 2d Ed., Pierce Chemical Company Rockford, Ill.; Ahmed et al., 1975, J. Biol. Chem. 250:8477-8482; and Pennington et al., 1991 Peptides 1990 164-166, Giralt and Andreu, Eds., ESCOM; Leiden, The Netherlands. An additional alternative is described by Kamber et al., 1980, Helv Chim Acta, 63:899-915. A method conducted on solid supports is described by Albericio, 1985, Int. J. Peptide Protein Res., 26:92-97. Any of these methods may be used to form disulfide linkages in the peptides of the invention. Preferred methods for effecting disulfide-bridge formation for the peptides described herein are provided in the examples.

If the peptide is composed entirely of gene-encoded amino acids, or a portion of it is so composed, the peptide or the relevant portion may also be synthesized using conventional recombinant genetic engineering techniques. The isolated peptides, or segments thereof, are then condensed, and oxidized, as previously described, to yield a cyclic peptide.

For recombinant production, a polynucleotide sequence encoding a linear form of the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the linear form of the cyclic peptide. Depending on the expression system used, the expressed peptide is then isolated by procedures well-established in the art. Methods for recombinant protein and peptide production are well known in the art (see, e.g., Maniatis et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y.).

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or robacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of baceriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genomes of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CAMV (Brisson et al., 1984, Nature 310: 511-514), or the coat protein promoter of TMV (Takamatsu et al., 1987, EMBO J., 6:307-311) may be used; alternatively, plant promoters such as the small subunit of RUBISCO (Coruzzi et al., 1984, EMBO J. 3:1671-1680; Broglie et al., 1984, Science 224:838-843) or heat shock promoters, e.g., soybean hsp17.5-E or hsp17.3-B (Gurley et al., 1986, Mol. Cell. Biol. 6:599-565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, Methods for Plant Molecular Biology, Academic Press, NY, Section VIII, pp. 421-463; and Grierson & Corey, 1988, Plant Molecular Biology, $2^{nd}$ Ed., Blackie, London, Ch. 7-9.

In one insect expression system that may be used to produce the peptides of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et all, 1983, J. Virol., 46:584; Smith, U.S. Pat. No. 4,215,051). Further examples of this expression system may be found in Current Protocols in Molecular Biology, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g. Region E1 or E3) will result in a recombinant virus that is viable and capable of expressing peptide in infected hosts. (e.g., See Logan & Shenk, 1984, Proc. Natl. Acad. Sci. USA 81:3655-3659). Alternatively, the vaccinia 7.5 K promoter may be used, (see, e.g., Mackett et al., 1982, Proc. Natl. Acad. Sci. USA, 79:7415-7419; Mackett et al., 1984, J. Virol., 49:857-864; Panicali et al., 1982, Proc. Natl. Acad. Sci. 79:4927-4931).

Other expression systems for producing linear or non-cyclized forms of the cyclic peptides of the invention will be apparent to those having skill in the art.

The peptides and peptide analogues of the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art.

For affinity chromatography purification, any antibody which specifically binds the peptides or peptide analogues may be used. For the production of antibodies, various host animals, including but not limited to rabbits, mice, rats, etc., may be immunized by injection with a linear or cyclic peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Duerin) and *Corynebacterium parvum*.

Monoclonal antibodies to a peptide may be prepared using any technique which provides for the production of antibody molecules by continuous cell lines in culture. These include but are not limited to the hybridoma technique originally described by Koehler and Milstein, 1975, Nature, 256:495-497; the human B-cell hybridoma technique, Kosbor et al., 1983, Immunology Today, 4:72; Cote et al., 1983, Proc. Natl. Acad. Sci., USA, 80:2026-2030 and the EBV-hybridoma technique (Cole et al., 1985, Monoclonal Antibodies and Cancer Therapy, Alan R. Liss, Inc., pp. 77-96 (1985)). In addition, techniques developed for the production of "chimeric antibodies" (Morrison et al., 1984, Proc. Natl. Acad. Sci., USA, 81: 6851-6855; Neuberger et al., 1984, Nature, 312:604-608; Takada et al., 1985, Nature, 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce cyclic peptide-specific single chain antibodies.

Antibody fragments which contain deletions of specific binding sites may be generated by known techniques. For example, such fragments include but are not limited to F(ab')$_2$ fragments, which can be produced by pepsin digestion of the antibody molecule and Fab fragments, which can be generated by reducing the disulfide bridges of the F(ab')$_2$ fragments. Alternatively, Fab expression libraries may be constructed (Huse et al., 1989, Science 246: 1275-1281) to allow rapid and easy identification of monoclonal Fab fragments with the desired specificity for the cyclic peptide of interest The antibody or antibody fragment specific for the desired cyclic peptide can be attached, for example, to agarose, and the antibody-agarose complex is used in immunochromatography to purify cyclic peptides of the invention. See, Scopes, 1984, Protein Purification Principles and Practice, Spriger-Verlag New York, Inc., NY, Livingstone, 1974, Methods Enzymology: Immunoaffinity Chromatography of Proteins 34:723-731.

The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiological acceptable carriers, diluents, excipients or auxiliaries which facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions, etc. as are well-known in the art.

Systemic formulations include those designed for administration by injection, e.g. subcutaneous, intravenous, intramuscular, intrathecal or intrapertoneal injection, as well as those designed for transdermal, transmucosal, oral or pulmonary administration.

For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium, carboxymethylcellulose, and/or polyvinylpyrrolidone (PVP); granulating agents; and binding agents. If desired, disintegrating agents may be added, such as the cross-linked polyvinylpyrrolidone, atgar, or alginic acid or a salt thereof such as sodium alginate.

If desired, solid dosage forms may be sugar-coated or enteric-coated using standard techniques.

For oral preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or my intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutically acceptable salts are those salts which substantially retain the antimicrobial activity of the free bases and which are prepared by reaction with inorganic acids. Pharmaceutical salts tend to be more soluble in aqueous and other protic solvents than are the corresponding free base forms.

The compounds of the invention will generally be used in an amount effective to achieve the intended purpose. For use to prevent osteoclastogenesis and/or osteoclast activity, the compounds of the invention, or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulation a dosage range that is not toxic for use in human. The dosage of the compounds described herein lies preferably within a range of circulating concentrations that include the effective dose with little or not toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1).

The invention having been described, the following examples are offered by way of illustration and not limitation.

EXAMPLES

Example 1

Recently, therapeutic peptidomimetics that interfere with the TNF/TNF receptor (1) interaction have been developed based on atomic structures deduced from the crystal structures of TNF-α and the TNFβ/TNF receptor (1) complex (Takasaki et al. Nature Biotechnology, 15:1266-1270, 1997). The most critical TNF-α recognition site was localized to the first loop of the third domain of TNF receptor (1) (residues 107-114). A peptidomimetic (WP9QY) engineered to mimic this recognition site efficiently antagonized the effects of TNF-binding to the TNF-α receptor (1) in L929 lymphocytes.

This peptide (5-500 µM) was tested for its effect on osteoclast formation using the co-culture system induced by 1,250H2D3 and PGE2. Osteoclastogenesis was dose- and time-dependently inhibited by the peptide ($IC_{50}$=250 µM) but the $IC_{50}$ was 50-fold higher than what was required for the TNF/TNF receptor (1) interaction (5 µM). This difference suggests that the peptide inhibits osteoclastogenesis by interfering not with the TNF/TNF receptor (1) interaction but with another related ligand-receptor pair such as TRANCE/RANK. This was confirmed by demonstrating that WP9QY inhibits TRANCE-induced marrow cultures. There was a reciprocal dose-dependence of WP9QY and TRANCE. Thus, WP9QY is capable of interfering not only with TNF/TNF receptor (1) interaction but also with RANK Ligand/RANK interaction, thereby decreasing the osteoclastogenic potential of this cytokine.

TRANCE/RANK inhibitors of the invention may be evaluated for their ability to inhibit osteoclastogenesis and osteoclast function using the assay described herein.

Example 2

Identification of Osteoclasts Formed in Vitro

TRAP refers to tartrate resistant acid phosphatase which identifies osteoclast like cells.

Osteoprotegerin (OPG) is a naturally occurring secreted protein with homology to members of the TNF receptor family. Administration of OPG in vivo inhibits osteoclastogenesis and associated bone resorption and blocks the pathological increase in osteoclast numbers and activity seen in animal models that mimic osteopenic disorders in humans. OPG can be used as a positive control in the TRAP assay.

Cytochemical staining for TRAP is widely used for identifying osteoclasts in vivo and in vitro. Naphthol AS-MX phosphate 5 mg. Sigma, St. Louis, Mo.) is resolved in 0.5 ml of N,N-dimethylformamide (Wako). Thirty milligrams of fast red violet LB salt (Sigma) and 50 ml of 0.1 M sodium acetate buffer (pH 5.0) containing 50 mM sodium tartratet are added to the mixture (the TRAP-staining solution). Cells are fixed with 3.7% (v/v) formaldehyde in $Ca^{2-}$- and $Mg^{2+}$-free phosphate-buffered saline [PBS(−)] for 10 min. fixed again with ethanol-acetone (50:50, v:v) for 1 min. and incubated with the TRAP-staining solution for 10 min. at room temperature. TRAP-positive osteoclasts appear as red cells. The incubation period longer than 10 min. should be avoided since cells other than osteoclasts become weakly positive with time. After staining, cells are washed with distilled water, and TRAP-positive multinucleated cells having three or more nuclei are counted as osteoclasts under a microscope. (G. C. Nicholson, J. M. Mosely, P. M. Sexton, F. A. O. Mendelssohn, and T. J. Martin, *J. Clin. Invest.* 78, 355 (1986), which is incorporated herein by reference).

FORMULAE

FORMULA I

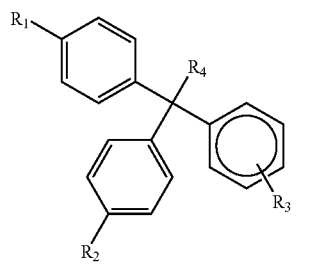

FORMULA II

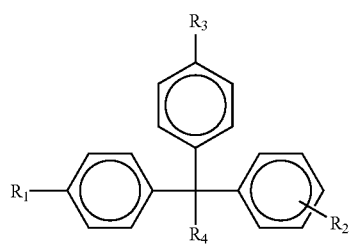

IA

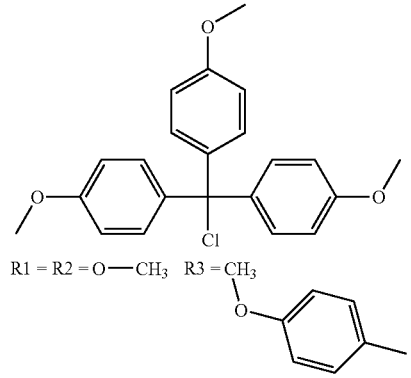

$R1 = R2 = O-CH_3$  $R3 = CH_3$

IB

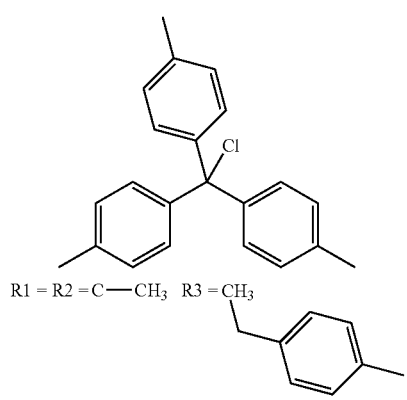

$R1 = R2 = C-CH_3$  $R3 = CH_3$

IC

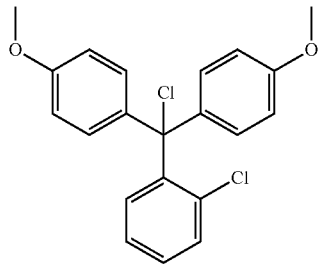

$R1 = R2 = O-CH_3$  $R3 =$

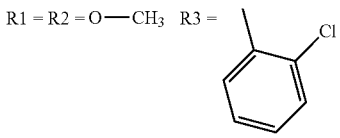

ID

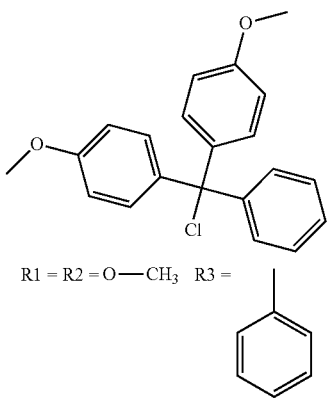

$R1 = R2 = O-CH_3$  $R3 =$

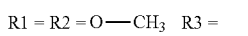

IE

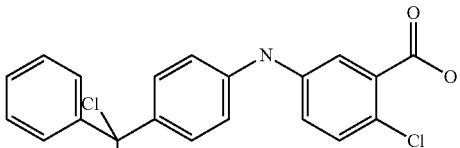

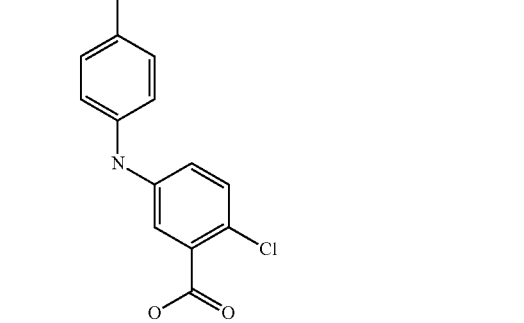

$R1 = H_2N$

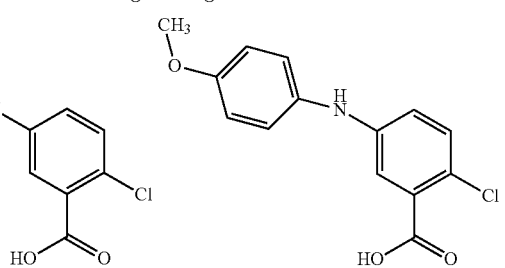

IF
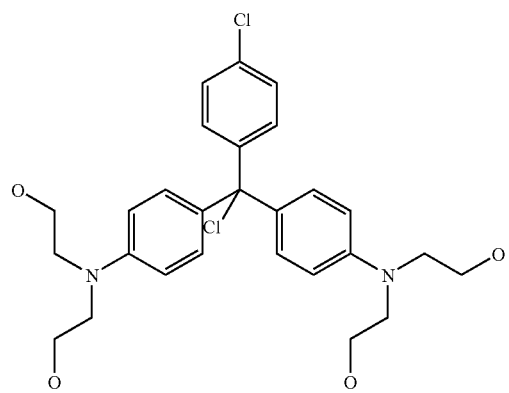
R1 = R2 = OH    R3 =
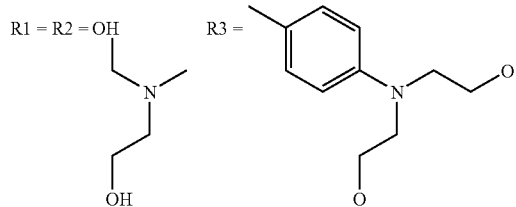
IG
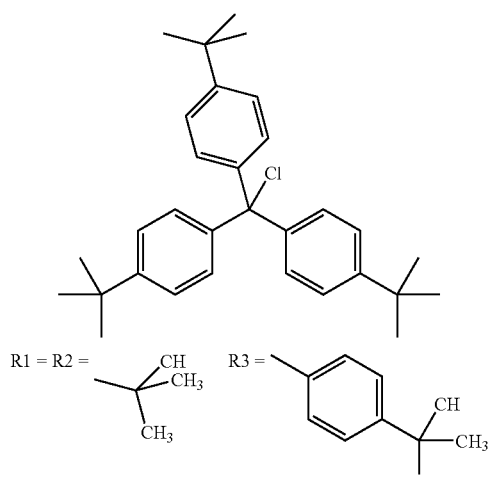
IH
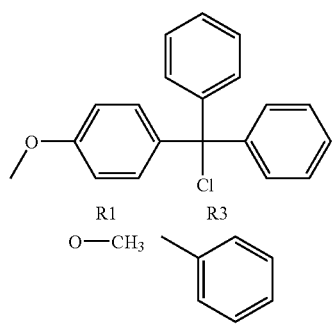
II
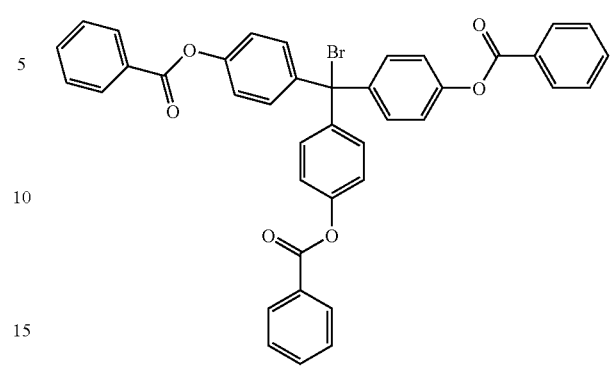
R1 = R2 =    R3 =
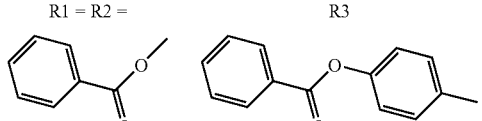
FORMULA II-A
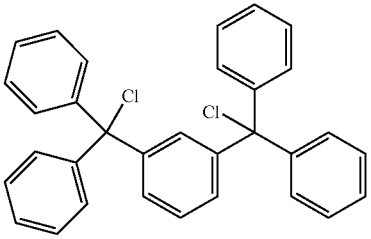
FORMULA II-B
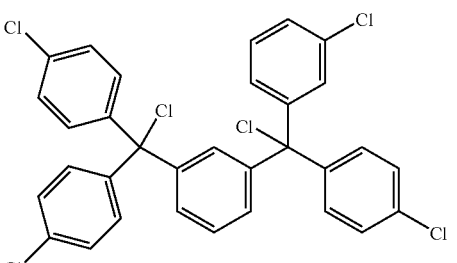
FORMULA II-C
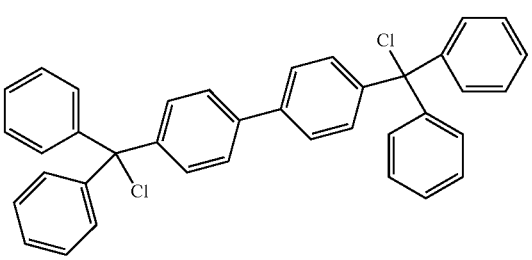
FORMULA II-D
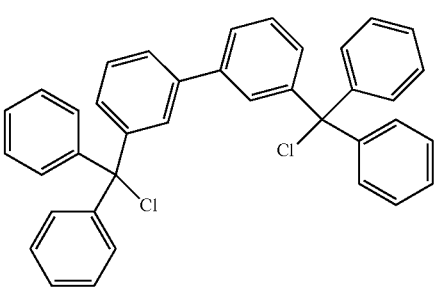

FORMULA III
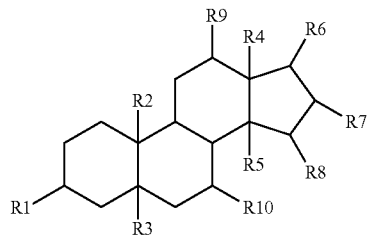
FORMULA IV
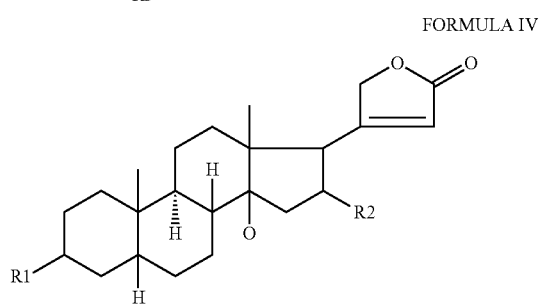
FORMULA V
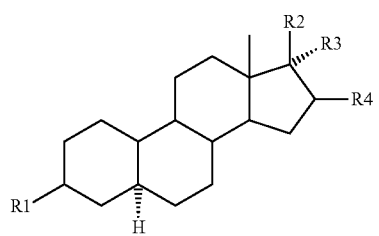
FORMULA VI
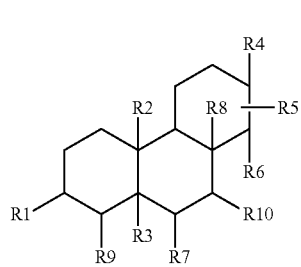
FORMULA III-1
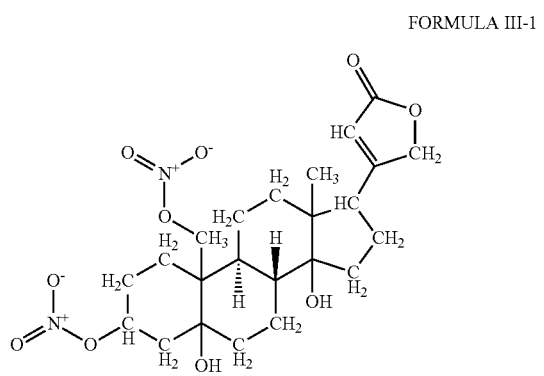
FORMULA III-2
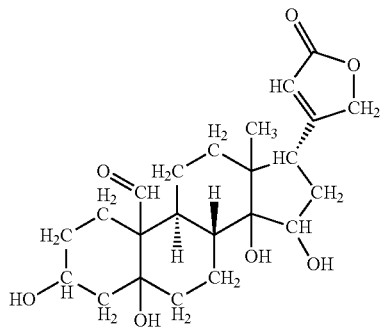
FORMULA III-3
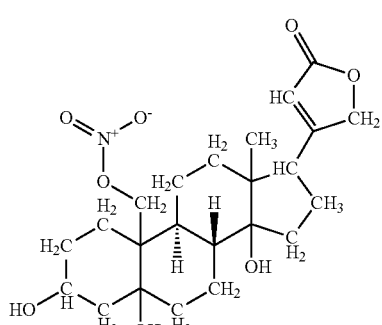
FORMULA III-4
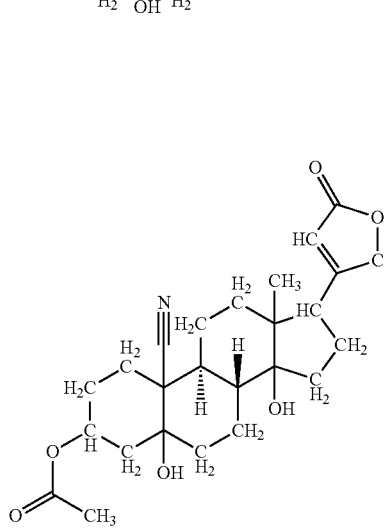
FORMULA III-5
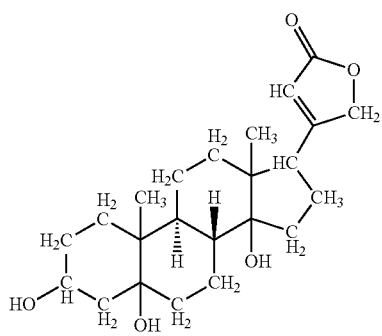

FORMULA III-6
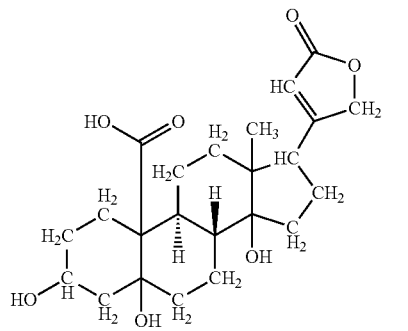
FORMULA III-7
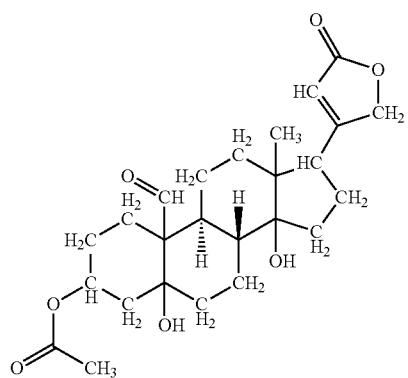
FORMULA III-8
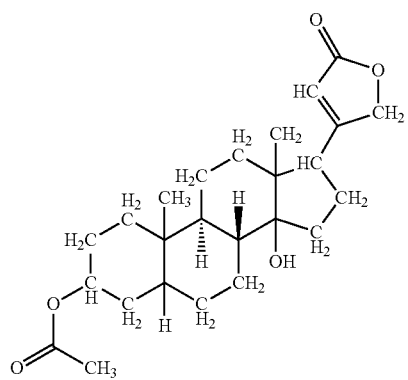
FORMULA III-9
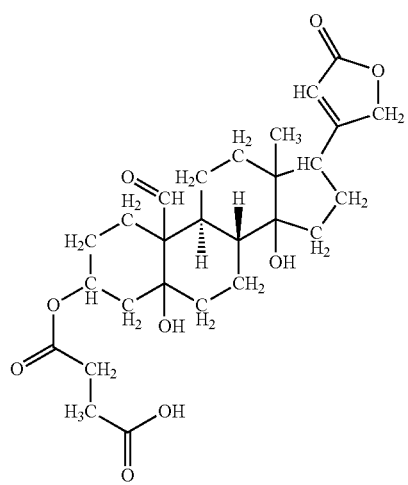
FORMULA III-10
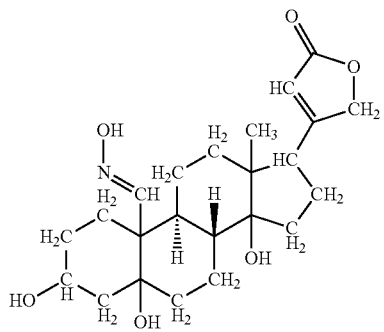
FORMULA III-11
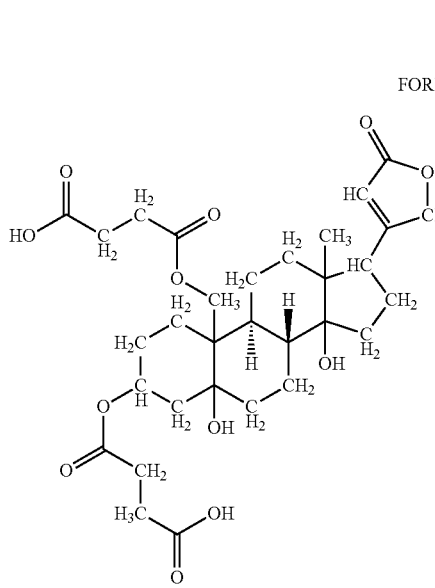
FORMULA III-12
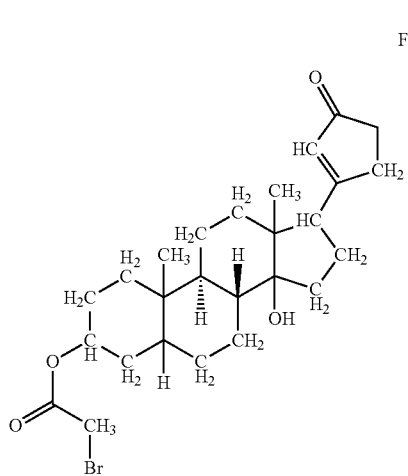

FORMULA III-13
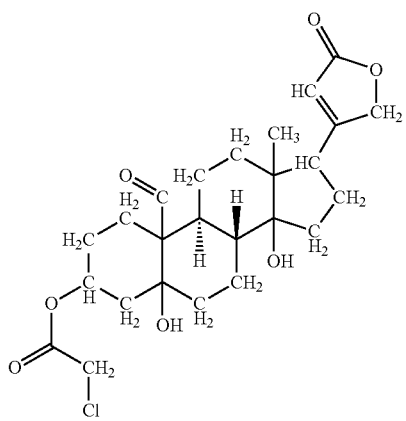
FORMULA III-14
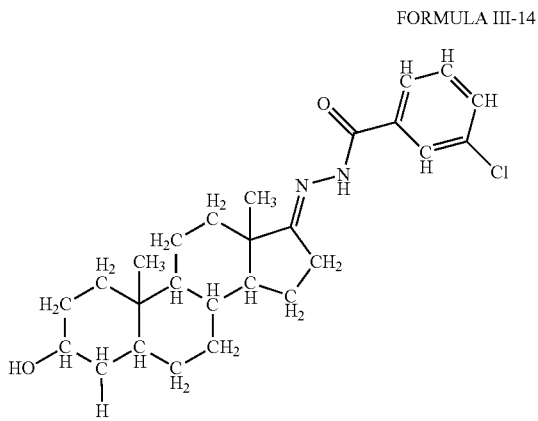
FORMULA III-15
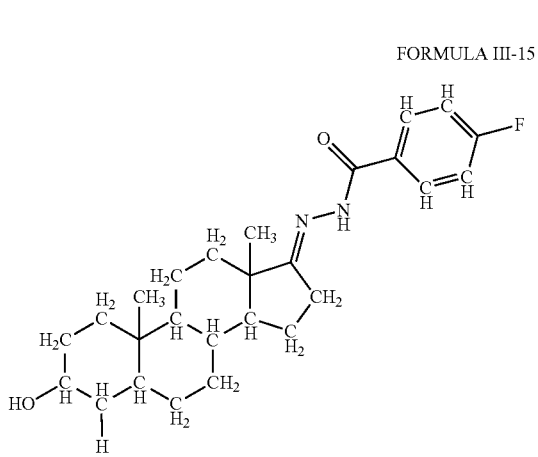
FORMULA III-16
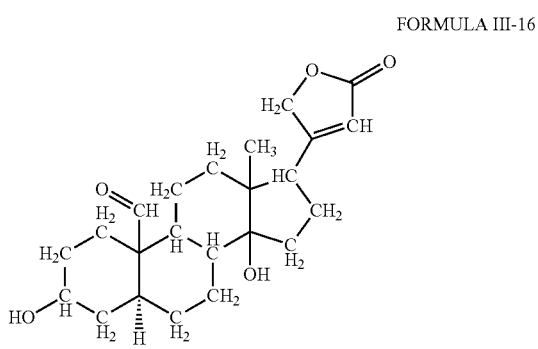
FORMULA III-17
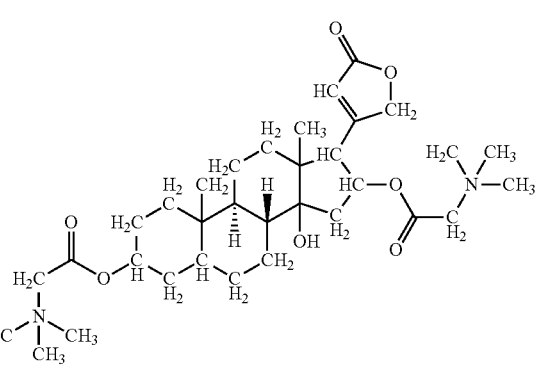
FORMULA III-18
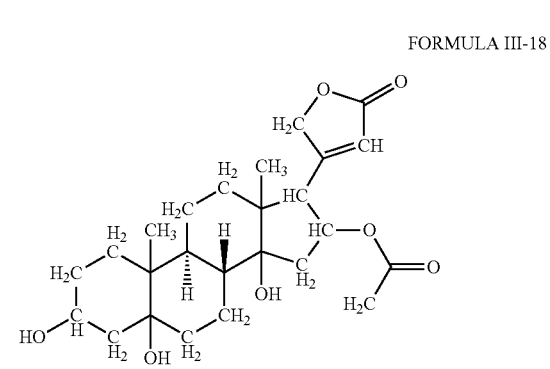
FORMULA III-19
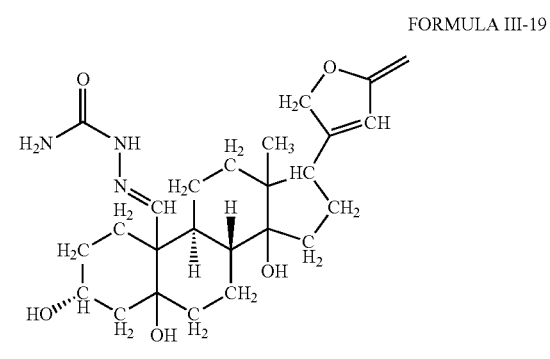
FORMULA III-20
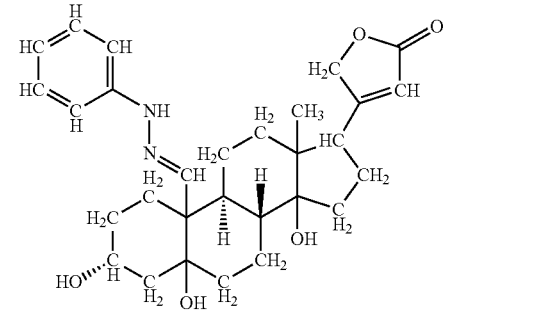

FORMULA III-21
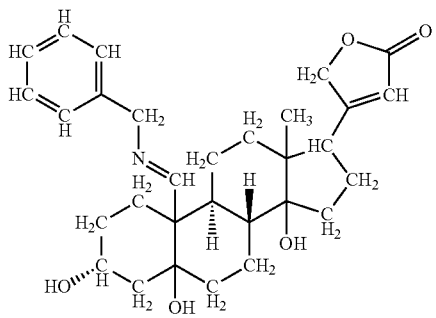
FORMULA III-22
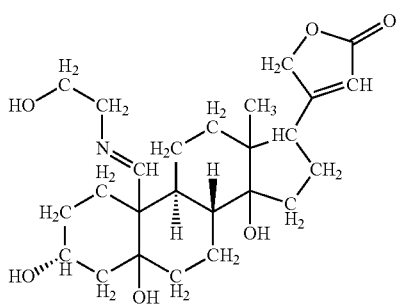
FORMULA III-23
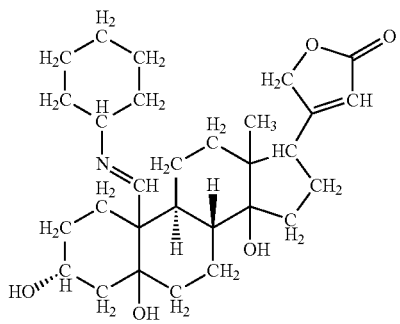
FORMULA III-24
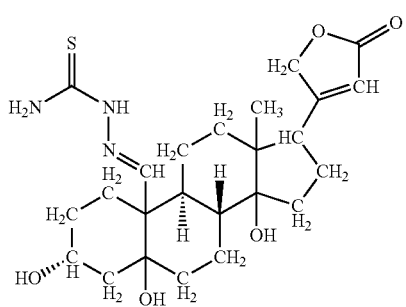
FORMULA III-25
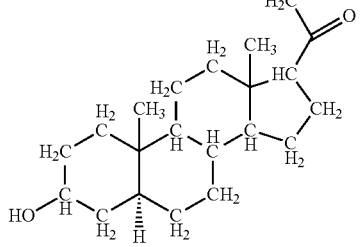
FORMULA III-26
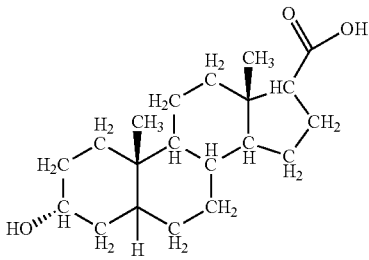
FORMULA III-27
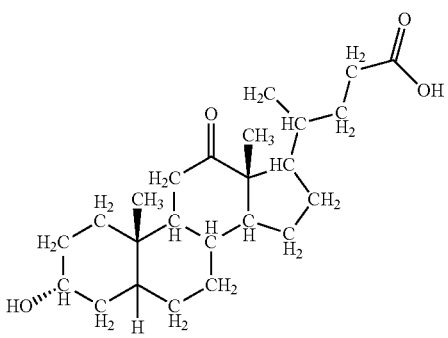
FORMULA III-28
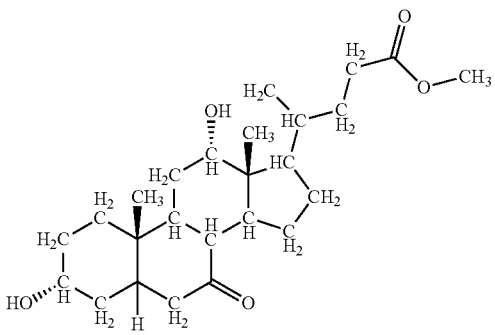
FORMULA III-29
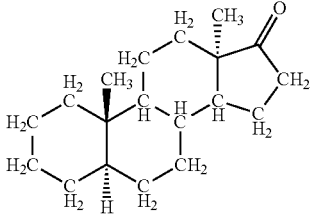
FORMULA III-30
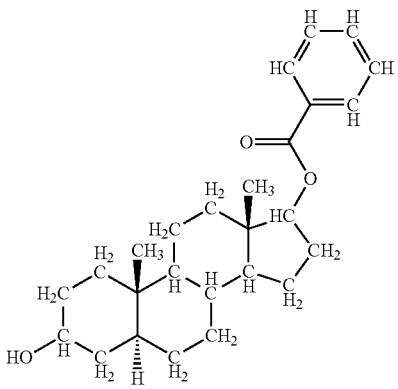

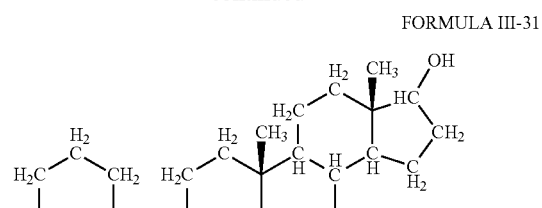

FORMULA VI-1
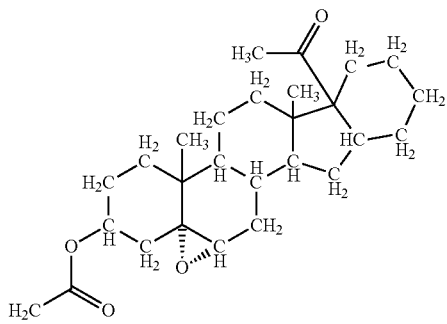
FORMULA VI-2
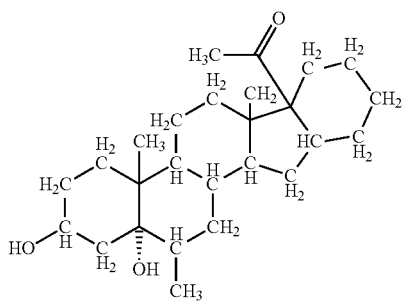
FORMULA VI-3
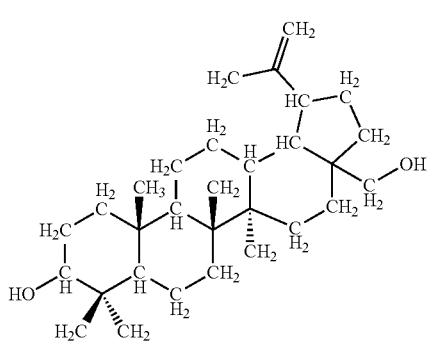
FORMULA VI-4
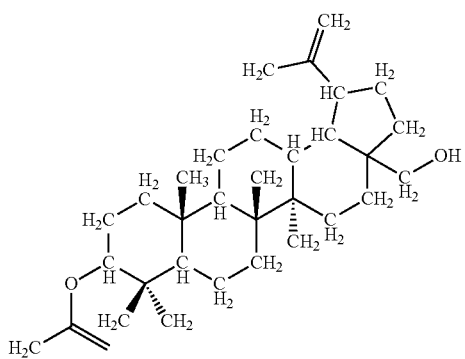
FORMULA VI-5
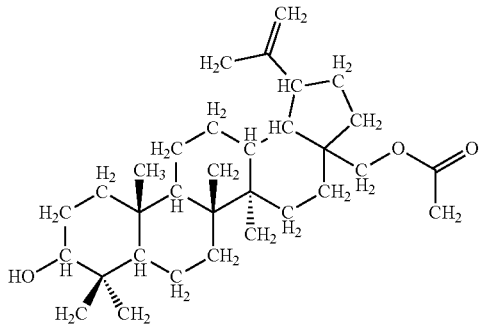
FORMULA VI-6
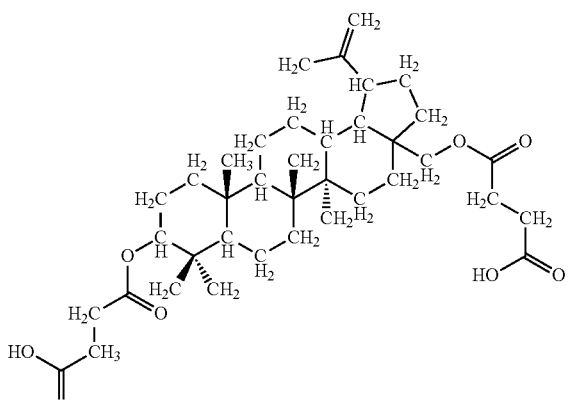
FORMULA VI-7
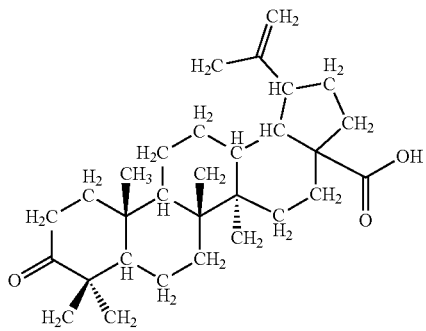
FORMULA VI-8
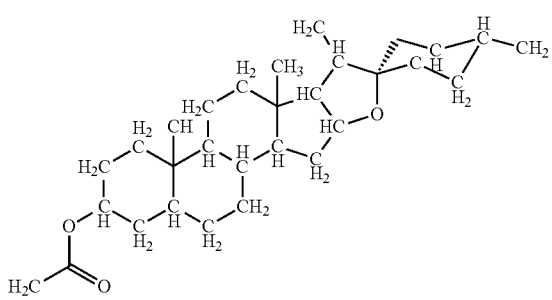

FORMULA VI-9
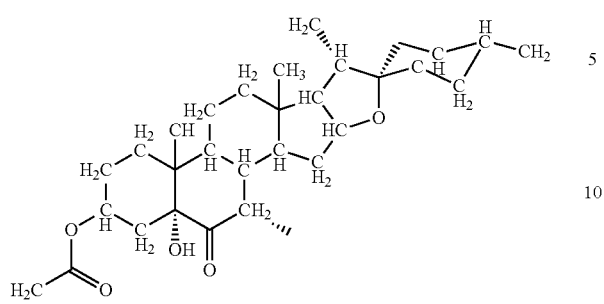
FORMULA VI-10
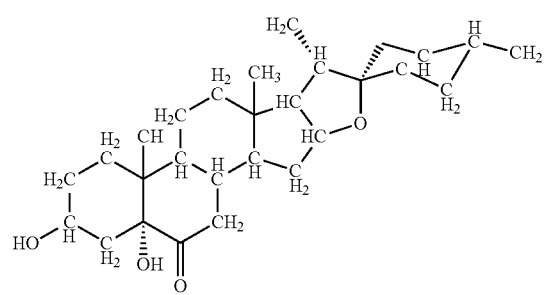
FORMULA VI-11
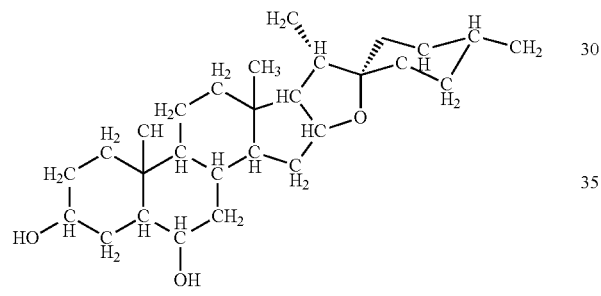
FORMULA VII
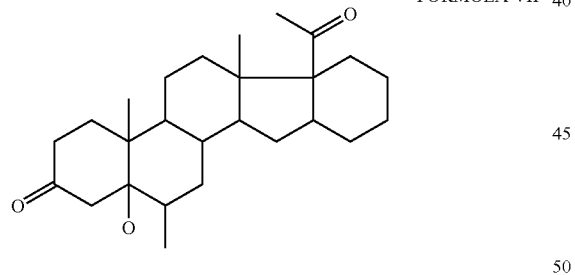
FORMULA VIII
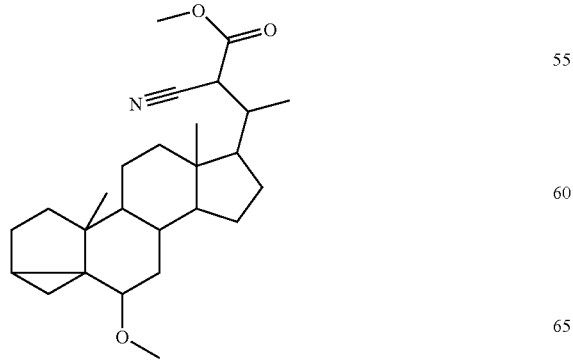
FORMULA IX
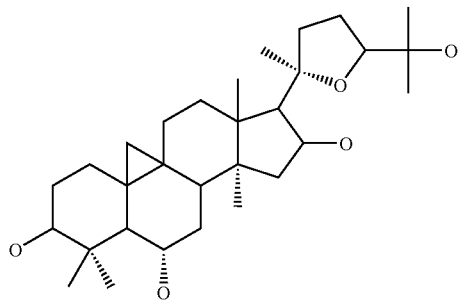
FORMULA X
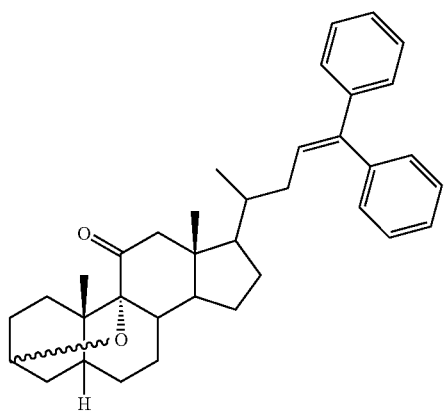
FORMULA XI
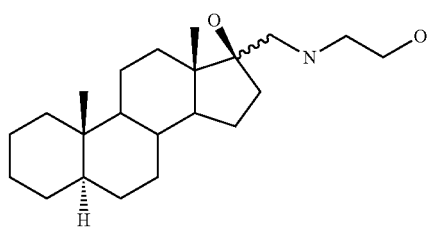
FORMULA XII
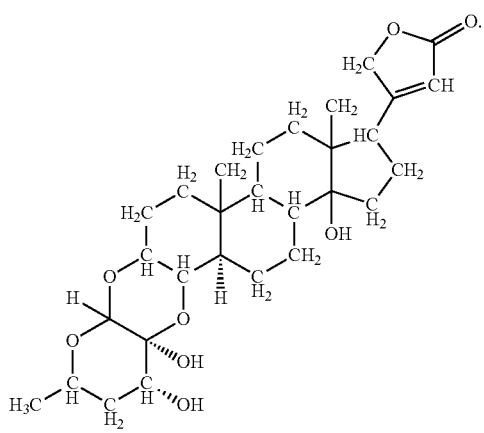

The invention claimed is:

1. A method of treating a patient who has a disease characterized by bone loss comprising the step of administering to said patient an amount of a TRANCE/RANK inhibitor effective to inhibit osteoclastogenesis and/or osteoclast function, wherein said inhibitor is a compound having Formula III

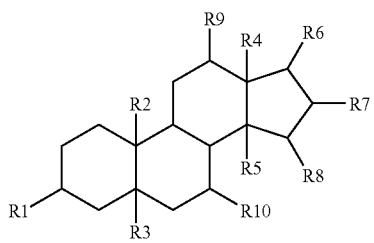

Formula III wherein:

$R_1$=H, $O(NO_2)$, $O(CO)CH_3$, OH, $O(CO)(CH_2)_2COOH$, $O(CO)CH_2Br$, $O(CO)CH_2Cl$, $O(CO)CH_2N(CH_3)_3$, or $OC_5H_9O$;

$R_2$=$CH_2O(NO_2)$, CHO, $CH_2O(NO_2)$, CN, $CH_3$, COOH, CHNOH, $CH_2O(CO)(CH_2)_2COOH$, CHN(NH)$CONH_2$, CHN(NH)$C_6H_5$, CHN($CH_2$)$C_6H_5$, $CH_2N(CH_2)_2OH$, $CH_2NC_6H_5$, or CHN(NH)$CSNH_2$;

$R_3$=OH, or H;

$R_4$=$CH_3$;

$R_5$=OH or H;

$R_6$=$C_4H_3O_2$, N(NHCO)$C_6H_4Cl$, N(NHCO)$C_6H_4F$, COOH, O, $COCH_3$, $CH(CH_3)(CH_2)_2COOH$, $CH(CH_3)(CH_2)_2COOCH_3$, $O(CO)C_6H_5$, or OH;

$R_7$=H, $O(CO)CH_2N(CH_3)_3$, or $O(CO)CH_3$;

$R_8$=OH or H;

$R_9$=H, O, or OH; and $R_{10}$=O or H.

2. The method of claim 1 wherein the inhibitor is a compound having a formula

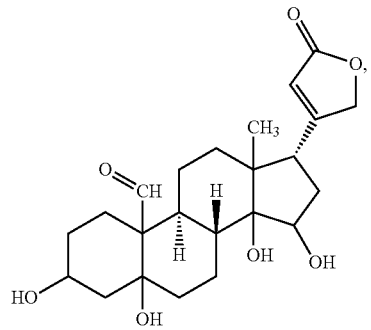

III-1

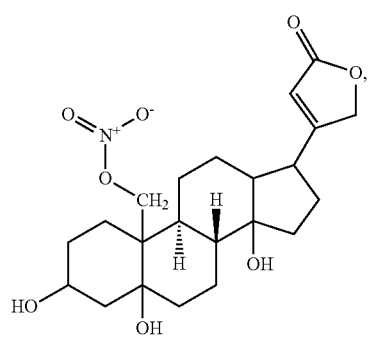

III-2

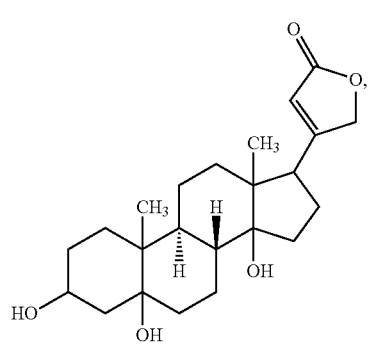

III-3

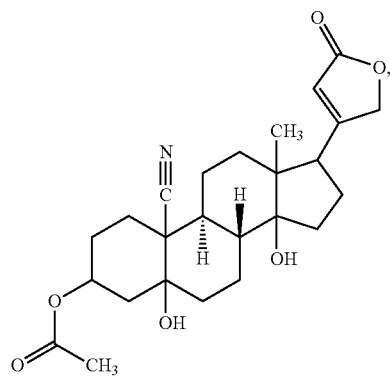

III-5

III-4

III-6
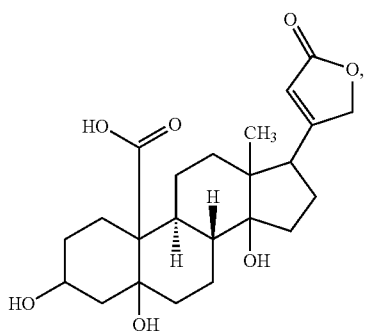
III-7
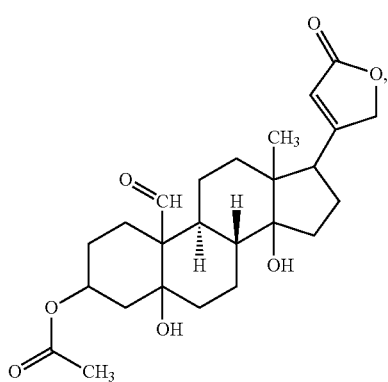
III-8
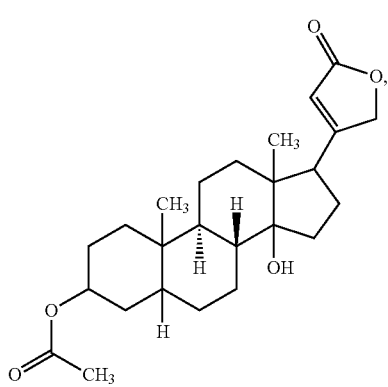
III-9
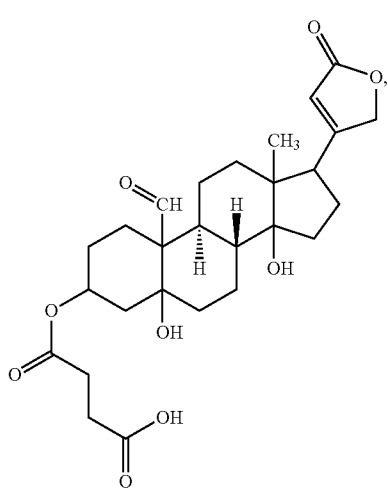
III-10
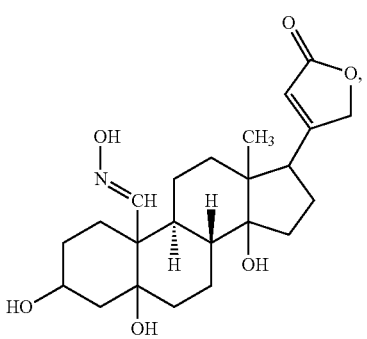
III-11
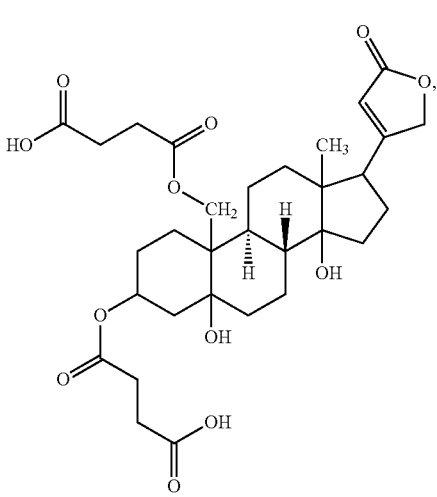
III-12
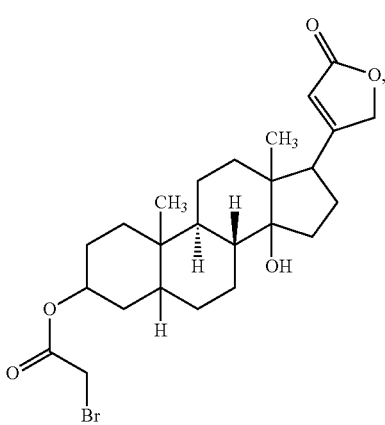
III-13
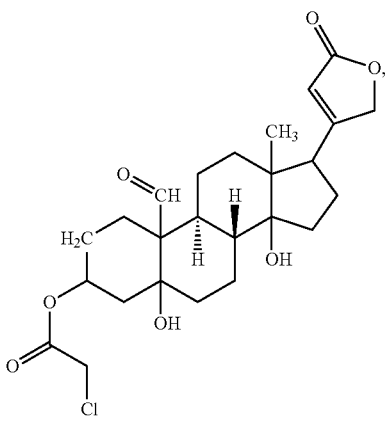

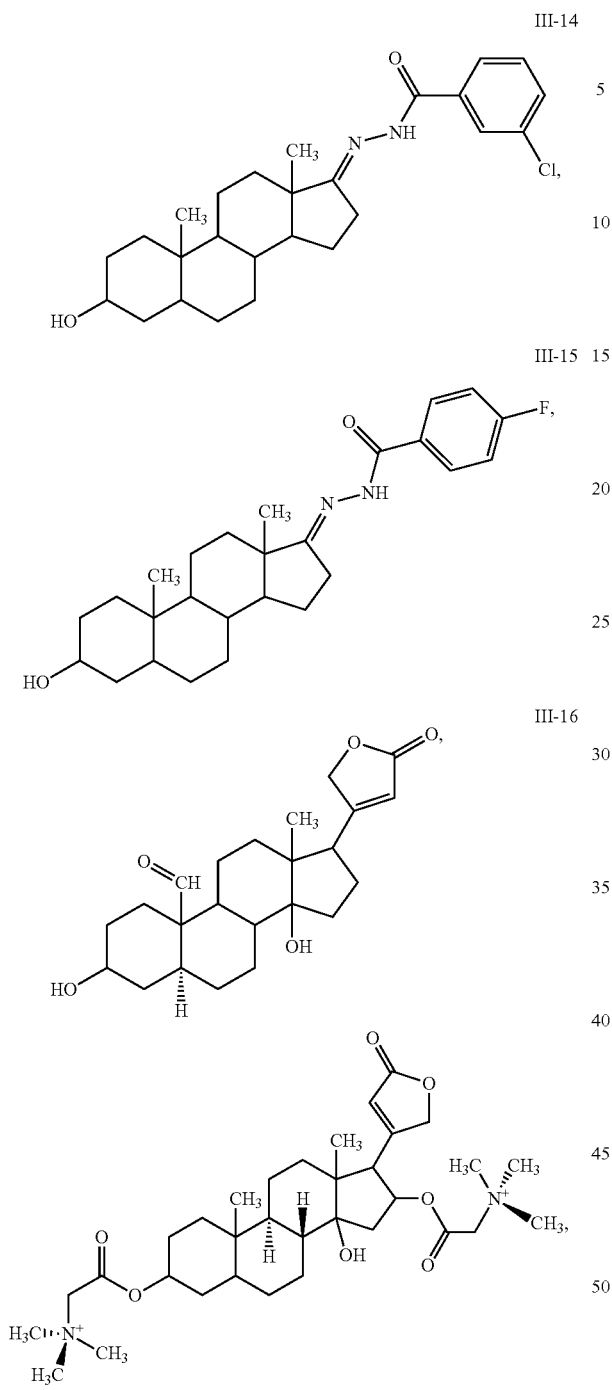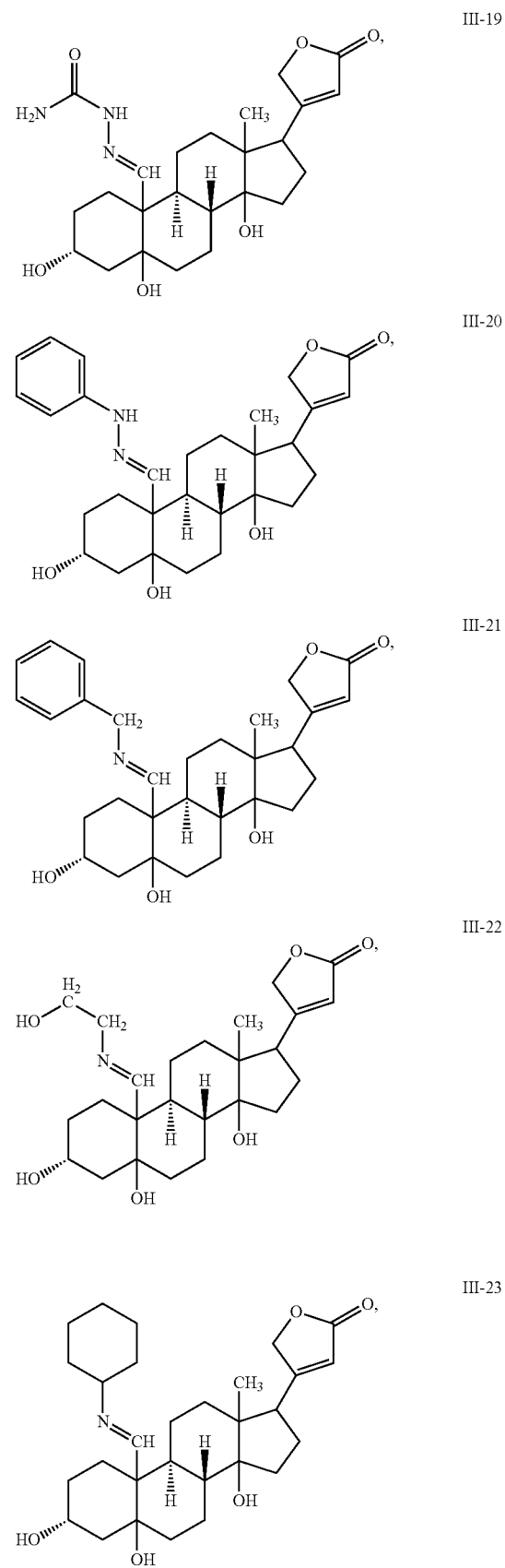

III-24
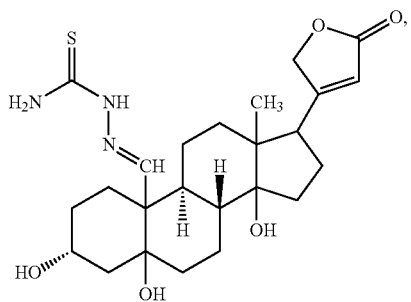

III-25
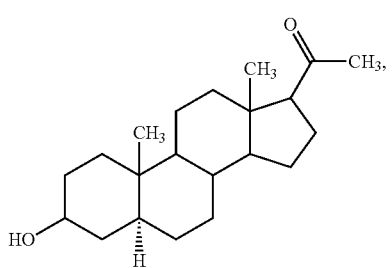

III-26
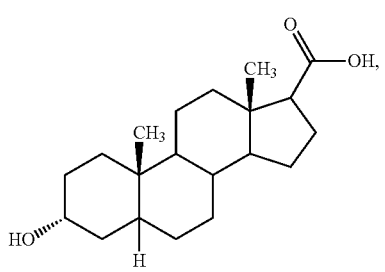

III-27
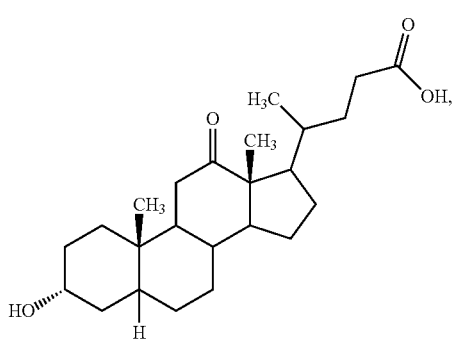

III-28
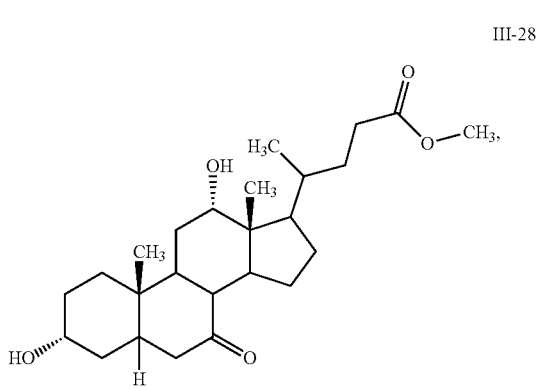

III-29
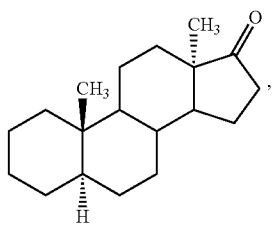

III-30
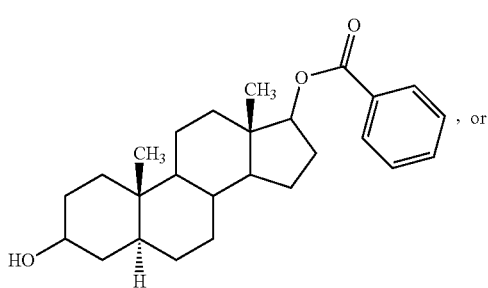

, or

III-31
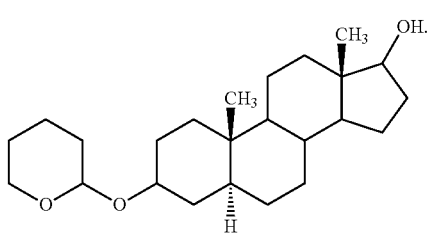

3. A method of treating a patient who has a disease characterized by bone loss comprising the step of administering to said patient an amount of a TRANCE/RANK inhibitor effective to inhibit osteoclastogenesis and/or osteoclast function, wherein said inhibitor is a compound having Formula IV:

Formula IV
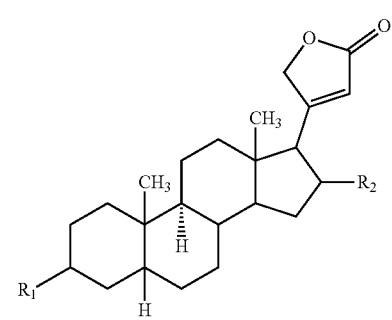

wherein:
R1=O(CO)(CH$_2$)$_2$COOH, or O(CO)CH$_2$Br; and
R2=O(CO)(CH$_2$)$_2$COOH, or O(CO)CH$_2$Br.

4. The method of claim 3 wherein the inhibitor is a compound having a formula

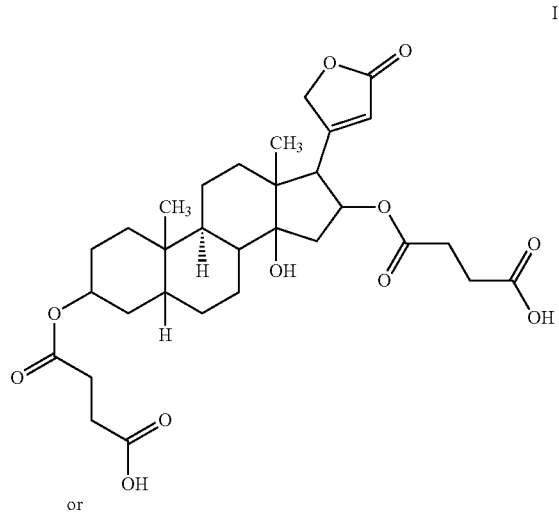

IV-1 or

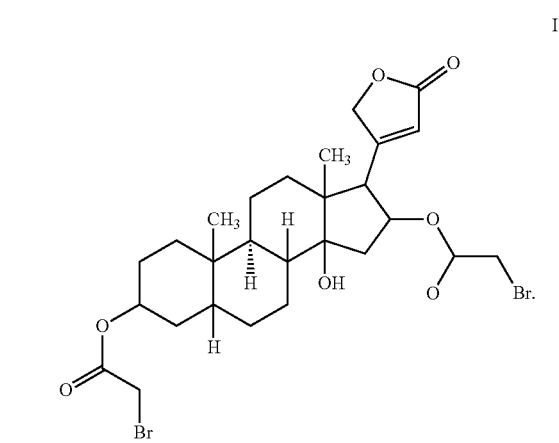

IV-2

5. A method of treating a patient who has a disease characterized by bone loss comprising the step of administering to said patient an amount of a TRANCE/RANK inhibitor effective to inhibit osteoclastogenesis and/or osteoclast function, wherein said inhibitor is a compound having Formula V

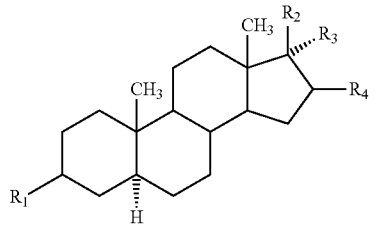

Formula V wherein:
  $R_1$=O, OH, or O(CO)CH$_3$:
  $R_2$=O(CO)CH$_3$, OH, CO(CH$_3$), or CO(CH$_2$)O(CO)CH$_3$;
  $R_3$=CH$_3$, or OH; and
  $R_4$=H, O(CO)CH$_2$C$_6$H$_4$I, or CH$_3$.

6. The method of claim 5, wherein the inhibitor is a compound having a formula

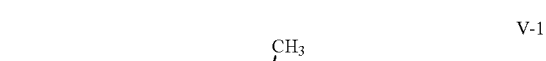

V-1

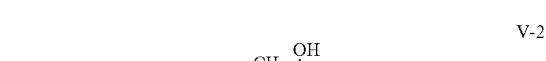

V-2

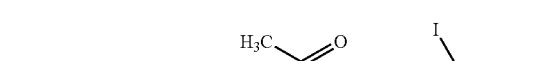

V-3

V-4

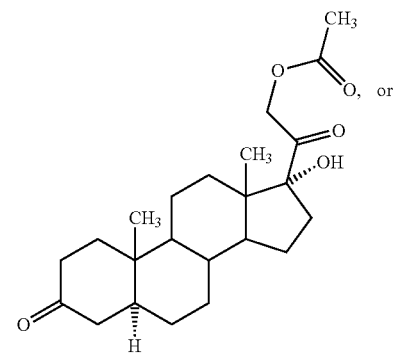

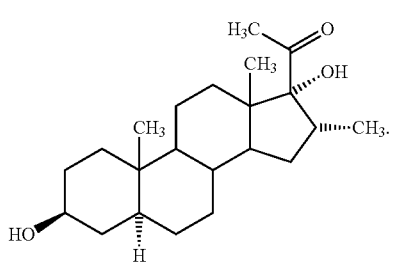
V-5
7. A method of treating a patient who has a disease characterized by bone loss comprising the step of administering to said patient an amount of a TRANCE/RANK inhibitor effective to inhibit osteoclastogenesis and/or osteoclast function, wherein the inhibitor is a compound having a formula
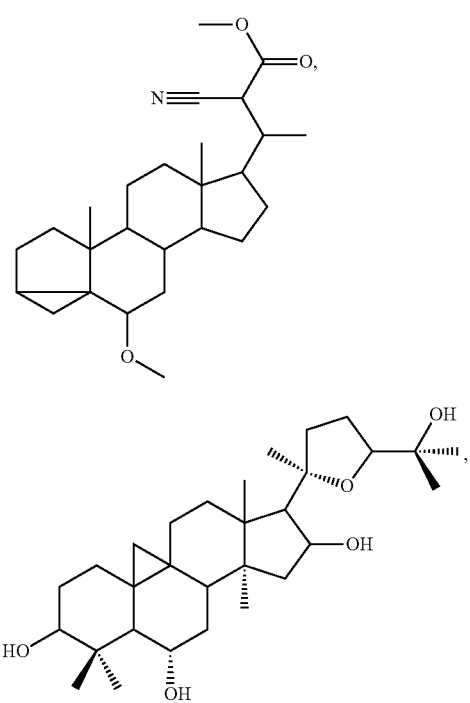
VIII
IX
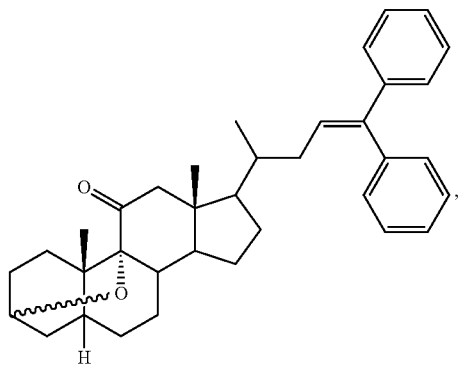
X
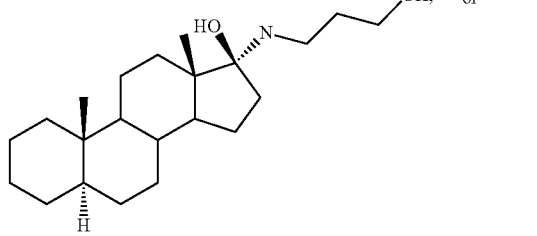
XI or
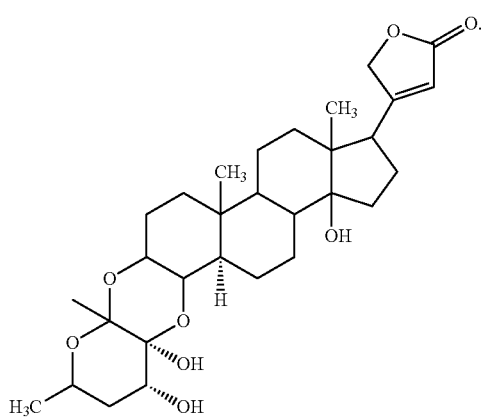
XII
* * * * *